United States Patent
Giorgi et al.

(10) Patent No.: US 7,402,394 B2
(45) Date of Patent: Jul. 22, 2008

(54) CENTROSOME-ASSOCIATED PROTEIN AND APPLICATIONS THEREOF

(75) Inventors: Dominique Giorgi, Saint Gely du Fesc (FR); Sylvie Rouquier, Saint Gely du Fesc (FR); Jean-Michel Saffin, Montpellier (FR)

(73) Assignee: Centre National de la Recherche Scientifique, Paris (FR)

( * ) Notice: Subject to any disclaimer, the term of this patent is extended or adjusted under 35 U.S.C. 154(b) by 87 days.

(21) Appl. No.: 10/540,493

(22) PCT Filed: Dec. 24, 2003

(86) PCT No.: PCT/FR03/03895

§ 371 (c)(1),
(2), (4) Date: Jun. 24, 2005

(87) PCT Pub. No.: WO2004/058815

PCT Pub. Date: Jul. 15, 2004

(65) Prior Publication Data

US 2006/0216710 A1    Sep. 28, 2006

(30) Foreign Application Priority Data

Dec. 24, 2002    (FR) .................................. 02 16648

(51) Int. Cl.
*G01N 33/53*    (2006.01)

(52) U.S. Cl. ........................................................ 435/7.1

(58) Field of Classification Search ....................... None
See application file for complete search history.

(56) References Cited

FOREIGN PATENT DOCUMENTS

WO    WO 00/73801    12/2000
WO    WO 02/070539    12/2002

OTHER PUBLICATIONS

STIC Sequence alignment, OM protein—protein search, using sw model Run on: Apr. 19, 2007, pp. 1-3.*
XP002252293, "*Homo sapiens* BAC clone RP11-27G13 from 4, complete sequence", Waterstone R.H., 1998.
XP-002288171, "*Homo sapiens* cDNA: FLJ21159 fis, clone CAS09969", Sugano S. et al., 1997.
XP-002288169, "Centrosomes and Cancer: lessons from a TACC," Jordan W. Raff, 1998.
XP-002288170, "Centromere proteins and chromosome inheritance: a complex affair", Kenneth W. Dobie et al., 2000.
XP-002307713, "*Mus musculus* adult male pituitary gland cDNA,", 1998.
XP-002307714, "*Mus musculus* Riken cDNA 5330427D05 gne, mRNA (cDNA clone IMAGE: 30254438) partial cds", 1999.

* cited by examiner

*Primary Examiner*—Robert B Mondesi
(74) *Attorney, Agent, or Firm*—William E. Beaumont

(57) ABSTRACT

The invention relates to a novel centrosome-associated protein, to the polynucleotide coding for the aforementioned protein and to the applications of said protein and polynucleotide. The overexpression of the inventive protein disrupts the mitotic spindle assembly and leads to aberrant and abortive mitoses.

9 Claims, 5 Drawing Sheets

A B C

SEQUENCE LISTING

<160> NUMBER OF SEQ ID NOS: 53

<210> SEQ ID NO 1
<211> LENGTH: 647
<212> TYPE: PRT
<213> ORGANISM: Homo sapiens

<400> SEQUENCE: 1

Met Ser Asp Glu Val Phe Ser Thr Thr Leu Ala Tyr Thr Lys Ser Pro
 1               5                  10                  15

Lys Val Thr Lys Arg Thr Thr Phe Gln Asp Glu Leu Ile Arg Ala Ile
             20                  25                  30

Thr Ala Arg Ser Ala Arg Gln Arg Ser Ser Glu Tyr Ser Asp Asp Phe
         35                  40                  45

Asp Ser Asp Glu Ile Val Ser Leu Gly Asp Phe Ser Asp Thr Ser Ala
     50                  55                  60

Asp Glu Asn Ser Val Asn Lys Lys Met Asn Asp Phe His Ile Ser Asp
 65                  70                  75                  80

Asp Glu Glu Lys Asn Pro Ser Lys Leu Leu Phe Leu Lys Thr Asn Lys
                 85                  90                  95

Ser Asn Gly Asn Ile Thr Lys Asp Glu Pro Val Cys Ala Ile Lys Asn
            100                 105                 110

Glu Glu Glu Met Ala Pro Asp Gly Cys Glu Asp Ile Val Val Lys Ser
        115                 120                 125

Phe Ser Glu Ser Gln Asn Lys Asp Glu Glu Phe Glu Lys Asp Lys Ile
    130                 135                 140

Lys Met Lys Pro Lys Pro Arg Ile Leu Ser Ile Lys Ser Thr Ser Ser
145                 150                 155                 160

Ala Glu Asn Asn Ser Leu Asp Thr Asp Asp His Phe Lys Pro Ser Pro
                165                 170                 175

Trp Pro Arg Ser Met Leu Lys Lys Lys Ser His Met Glu Glu Lys Asp
            180                 185                 190

Gly Leu Glu Asp Lys Glu Thr Ala Leu Ser Glu Glu Leu Glu Leu His
        195                 200                 205

Ser Ala Pro Ser Ser Leu Pro Thr Pro Asn Gly Ile Gln Leu Glu Ala
    210                 215                 220

Glu Lys Lys Ala Phe Ser Glu Asn Leu Asp Pro Glu Asp Ser Cys Leu
225                 230                 235                 240

Thr Ser Leu Ala Ser Ser Ser Leu Lys Gln Ile Leu Gly Asp Ser Phe
                245                 250                 255

Ser Pro Gly Ser Glu Gly Asn Ala Ser Gly Lys Asp Pro Asn Glu Glu
            260                 265                 270

Ile Thr Glu Asn His Asn Ser Leu Lys Ser Asp Glu Asn Lys Glu Asn
        275                 280                 285

Ser Phe Ser Ala Asp His Val Thr Thr Ala Val Glu Lys Ser Lys Glu
    290                 295                 300

Ser Gln Val Thr Ala Asp Leu Glu Glu Lys Ala Lys Ala Glu
305                 310                 315                 320

Leu Ile Met Asp Asp Asp Arg Thr Val Asp Pro Leu Leu Ser Lys Ser
                325                 330                 335

Gln Ser Ile Leu Ile Ser Thr Ser Ala Thr Ala Ser Ser Lys Lys Thr
            340                 345                 350

Ile Glu Asp Arg Asn Ile Lys Asn Lys Lys Ser Thr Asn Asn Arg Ala

```
                 355                 360                 365
Ser Ser Ala Ser Ala Arg Leu Met Thr Ser Glu Phe Leu Lys Lys Ser
    370                 375                 380

Ser Ser Lys Arg Arg Thr Pro Ser Thr Thr Ser Ser His Tyr Leu
385                 390                 395                 400

Gly Thr Leu Lys Val Leu Asp Gln Lys Pro Ser Gln Lys Gln Ser Ile
                405                 410                 415

Glu Pro Asp Arg Ala Asp Asn Ile Arg Ala Ala Val Tyr Gln Glu Trp
                420                 425                 430

Leu Glu Lys Lys Asn Val Tyr Leu His Glu Met His Arg Ile Lys Arg
            435                 440                 445

Ile Glu Ser Glu Asn Leu Arg Ile Gln Asn Glu Gln Lys Lys Ala Ala
        450                 455                 460

Lys Arg Glu Glu Ala Leu Ala Ser Phe Glu Ala Trp Lys Ala Met Lys
465                 470                 475                 480

Glu Lys Glu Ala Lys Ile Ala Ala Lys Arg Leu Glu Glu Lys
                485                 490                 495

Asn Lys Lys Lys Thr Glu Glu Asn Ala Ala Arg Lys Gly Glu Ala
            500                 505                 510

Leu Gln Ala Phe Glu Lys Trp Lys Glu Lys Met Glu Tyr Leu Lys
        515                 520                 525

Glu Lys Asn Arg Lys Glu Arg Glu Tyr Glu Arg Ala Lys Lys Gln Lys
530                 535                 540

Glu Glu Glu Thr Val Ala Glu Lys Lys Lys Asp Asn Leu Thr Ala Val
545                 550                 555                 560

Glu Lys Trp Asn Glu Lys Lys Glu Ala Phe Phe Lys Gln Lys Lys Lys
                565                 570                 575

Glu Lys Ile Asn Glu Lys Arg Lys Glu Glu Leu Lys Arg Ala Glu Lys
            580                 585                 590

Lys Asp Lys Asp Lys Gln Ala Ile Asn Glu Tyr Glu Lys Trp Leu Glu
        595                 600                 605

Asn Lys Glu Lys Gln Glu Arg Ile Glu Arg Lys Gln Lys Lys Arg His
610                 615                 620

Ser Phe Leu Glu Ser Glu Ala Leu Pro Pro Trp Ser Pro Pro Ser Arg
625                 630                 635                 640

Thr Val Phe Ala Lys Val Phe
                645

<210> SEQ ID NO 2
<211> LENGTH: 25
<212> TYPE: PRT
<213> ORGANISM: Homo sapiens

<400> SEQUENCE: 2

Met Ser Asp Glu Val Phe Ser Thr Thr Leu Ala Tyr Thr Lys Ser Pro
1               5                   10                  15

Lys Val Thr Lys Arg Thr Thr Phe Gln
            20                  25

<210> SEQ ID NO 3
<211> LENGTH: 28
<212> TYPE: PRT
<213> ORGANISM: Homo sapiens

<400> SEQUENCE: 3

Asp Glu Leu Ile Arg Ala Ile Thr Ala Arg Ser Ala Arg Gln Arg Ser
```

```
                1               5                  10                  15
Ser Glu Tyr Ser Asp Asp Phe Asp Ser Asp Glu Ile
                        20                  25
```

<210> SEQ ID NO 4
<211> LENGTH: 107
<212> TYPE: PRT
<213> ORGANISM: Homo sapiens

<400> SEQUENCE: 4

```
Val Ser Leu Gly Asp Phe Ser Asp Thr Ser Ala Asp Glu Asn Ser Val
 1               5                  10                  15

Asn Lys Lys Met Asn Asp Phe His Ile Ser Asp Glu Glu Lys Asn
                20                  25                  30

Pro Ser Lys Leu Leu Phe Leu Lys Thr Asn Lys Ser Asn Gly Asn Ile
            35                  40                  45

Thr Lys Asp Glu Pro Val Cys Ala Ile Lys Asn Glu Glu Glu Met Ala
        50                  55                  60

Pro Asp Gly Cys Glu Asp Ile Val Val Lys Ser Phe Ser Glu Ser Gln
65                  70                  75                  80

Asn Lys Asp Glu Glu Phe Glu Lys Asp Lys Ile Lys Met Lys Pro Lys
                85                  90                  95

Pro Arg Ile Leu Ser Ile Lys Ser Thr Ser Ser
                100                 105
```

<210> SEQ ID NO 5
<211> LENGTH: 76
<212> TYPE: PRT
<213> ORGANISM: Homo sapiens

<400> SEQUENCE: 5

```
Ala Glu Asn Asn Ser Leu Asp Thr Asp Asp His Phe Lys Pro Ser Pro
 1               5                  10                  15

Trp Pro Arg Ser Met Leu Lys Lys Lys Ser His Met Glu Glu Lys Asp
                20                  25                  30

Gly Leu Glu Asp Lys Glu Thr Ala Leu Ser Glu Glu Leu Glu Leu His
            35                  40                  45

Ser Ala Pro Ser Ser Leu Pro Thr Pro Asn Gly Ile Gln Leu Glu Ala
        50                  55                  60

Glu Lys Lys Ala Phe Ser Glu Asn Leu Asp Pro Glu
65                  70                  75
```

<210> SEQ ID NO 6
<211> LENGTH: 31
<212> TYPE: PRT
<213> ORGANISM: Homo sapiens

<400> SEQUENCE: 6

```
Asp Ser Cys Leu Thr Ser Leu Ala Ser Ser Leu Lys Gln Ile Leu
 1               5                  10                  15

Gly Asp Ser Phe Ser Pro Gly Ser Glu Gly Asn Ala Ser Gly Lys
                20                  25                  30
```

<210> SEQ ID NO 7
<211> LENGTH: 83
<212> TYPE: PRT
<213> ORGANISM: Homo sapiens

<400> SEQUENCE: 7

```
Asp Pro Asn Glu Glu Ile Thr Glu Asn His Asn Ser Leu Lys Ser Asp
  1               5                  10                  15

Glu Asn Lys Glu Asn Ser Phe Ser Ala Asp His Val Thr Thr Ala Val
             20                  25                  30

Glu Lys Ser Lys Glu Ser Gln Val Thr Ala Asp Asp Leu Glu Glu
         35                  40                  45

Lys Ala Lys Ala Glu Leu Ile Met Asp Asp Asp Arg Thr Val Asp Pro
 50                  55                  60

Leu Leu Ser Lys Ser Gln Ser Ile Leu Ile Ser Thr Ser Ala Thr Ala
 65                  70                  75                  80

Ser Ser Lys

<210> SEQ ID NO 8
<211> LENGTH: 24
<212> TYPE: PRT
<213> ORGANISM: Homo sapiens

<400> SEQUENCE: 8

Lys Thr Ile Glu Asp Arg Asn Ile Lys Asn Lys Lys Ser Thr Asn Asn
  1               5                  10                  15

Arg Ala Ser Ser Ala Ser Ala Arg
             20

<210> SEQ ID NO 9
<211> LENGTH: 54
<212> TYPE: PRT
<213> ORGANISM: Homo sapiens

<400> SEQUENCE: 9

Leu Met Thr Ser Glu Phe Leu Lys Lys Ser Ser Lys Arg Arg Thr
  1               5                  10                  15

Pro Ser Thr Thr Thr Ser Ser His Tyr Leu Gly Thr Leu Lys Val Leu
             20                  25                  30

Asp Gln Lys Pro Ser Gln Lys Gln Ser Ile Glu Pro Asp Arg Ala Asp
         35                  40                  45

Asn Ile Arg Ala Ala Val
         50

<210> SEQ ID NO 10
<211> LENGTH: 32
<212> TYPE: PRT
<213> ORGANISM: Homo sapiens

<400> SEQUENCE: 10

Tyr Gln Glu Trp Leu Glu Lys Lys Asn Val Tyr Leu His Glu Met His
  1               5                  10                  15

Arg Ile Lys Arg Ile Glu Ser Glu Asn Leu Arg Ile Gln Asn Glu Gln
             20                  25                  30

<210> SEQ ID NO 11
<211> LENGTH: 54
<212> TYPE: PRT
<213> ORGANISM: Homo sapiens

<400> SEQUENCE: 11

Lys Lys Ala Ala Lys Arg Glu Glu Ala Leu Ala Ser Phe Glu Ala Trp
  1               5                  10                  15

Lys Ala Met Lys Glu Lys Glu Ala Lys Lys Ile Ala Ala Lys Lys Arg
             20                  25                  30
```

Leu Glu Glu Lys Asn Lys Lys Lys Thr Glu Glu Glu Asn Ala Ala Arg
    35                  40                  45

Lys Gly Glu Ala Leu Gln
    50

<210> SEQ ID NO 12
<211> LENGTH: 49
<212> TYPE: PRT
<213> ORGANISM: Homo sapiens

<400> SEQUENCE: 12

Ala Phe Glu Lys Trp Lys Glu Lys Lys Met Glu Tyr Leu Lys Glu Lys
1               5                   10                  15

Asn Arg Lys Glu Arg Glu Tyr Glu Arg Ala Lys Lys Gln Lys Glu Glu
                20                  25                  30

Glu Thr Val Ala Glu Lys Lys Lys Asp Asn Leu Thr Ala Val Glu Lys
            35                  40                  45

Trp

<210> SEQ ID NO 13
<211> LENGTH: 43
<212> TYPE: PRT
<213> ORGANISM: Homo sapiens

<400> SEQUENCE: 13

Asn Glu Lys Lys Glu Ala Phe Phe Lys Gln Lys Lys Lys Glu Lys Ile
1               5                   10                  15

Asn Glu Lys Arg Lys Glu Glu Leu Lys Arg Ala Glu Lys Lys Asp Lys
                20                  25                  30

Asp Lys Gln Ala Ile Asn Glu Tyr Glu Lys Trp
            35                  40

<210> SEQ ID NO 14
<211> LENGTH: 41
<212> TYPE: PRT
<213> ORGANISM: Homo sapiens

<400> SEQUENCE: 14

Leu Glu Asn Lys Glu Lys Gln Glu Arg Ile Glu Arg Lys Gln Lys Lys
1               5                   10                  15

Arg His Ser Phe Leu Glu Ser Glu Ala Leu Pro Pro Trp Ser Pro Pro
                20                  25                  30

Ser Arg Thr Val Phe Ala Lys Val Phe
            35                  40

<210> SEQ ID NO 15
<211> LENGTH: 2575
<212> TYPE: DNA
<213> ORGANISM: Homo sapiens

<400> SEQUENCE: 15
acttccttcg tctgggtggt tgccccagcg acacgttggg ccgaagagcg gtgttgggta      60
cccgagagac ccggcggtgg ggaagtcact tcctcccgaa gacgctgttt cctagcaacc     120
gccctccgcc tctgttatta gcccctcctc ctcgctcggt ccaggaccgg ctctgcgggc     180
gccgccaggc ccagaccaag ctactatcag aagttgaatt ctaataatta gctattttat     240
aaaggtaacg agaaaaaata cactatgtct gatgaagttt ttagcaccac tttggcatat     300
acaaagagtc caaagttac caaagaact actttccagg atgagctaat aagagcaatt      360

```
acagctcgct cagccagaca aaggagttct gaatactcag atgactttga cagtgatgag    420
attgtttctt taggtgattt ttctgacact tcagcagatg aaaattcagt taataaaaaa    480
atgaatgact tcatatatc agatgatgaa gaaagaatc cttcaaaact attgtttttg      540
aaaaccaata aatcaaacgg taacataacc aaagatgagc cagtgtgtgc catcaaaaat    600
gaagaggaaa tggcacctga tgggtgtgaa gacattgttg taaaatcttt ctctgaatct    660
caaaataagg atgaggaatt tgaaaaagac aaaataaaaa tgaaacctaa acccagaatt    720
ctttcaatta aaagcacatc ttcagcagaa acaacagcc ttgacacaga tgatcacttt     780
aaaccatcac cttggccaag gagtatgtta aaaagaaaa gtcacatgga ggagaaggat     840
ggactagaag ataaagaaac tgccctcagt gaagaattgg agttacattc tgcaccttct    900
tcccttccaa cgccgaatgg catacaatta gaagctgaga aaaagcatt ctctgaaaac     960 cttgatcctg aggattcatg cttaacaagt ctagcatcat catcacttaa acaaattctt   1020
ggagattctt tttcaccagg atctgaggga acgcatctg gaaagatcc aaatgaagaa     1080 atcactgaaa accataattc cttgaaatca gatgaaaata agagaattc atttcagca    1140 gaccatgtga ctactgcagt tgagaaatcc aaggaaagtc aagtgactgc tgatgacctt   1200
gaagaagaaa aggcaaaagc ggaactgatt atggatgatg acagaacagt tgatccacta   1260
ctatctaaat ctcagagtat cttaatatct accagtgcaa cagcatcttc aaagaaaaca   1320
attgaagata gaaatataaa gaataaaaag tcaacaaata atagagcatc cagtgcatct   1380
gccagattaa tgacctctga gttttttgaag aaatctagtt ctaaaaggag aactccatcg   1440
acaactacct cttctcacta tttagggact ttaaaagtct tggaccaaaa accttcacag   1500
aaacagagca tagaacctga tagagcgat aacataaggg cagctgttta tcaggagtgg   1560
ttagaaaaga aaatgtata tttacatgaa atgcacagaa taaaaagaat tgaaagtgaa   1620
aacttaagga tccaaaatga acagaaaaaa gctgctaaaa gagaagaagc attagcatca   1680
tttgaggcct ggaaggctat gaaagaaaag gaagcaaaga aaatagctgc caaaaagagg   1740
cttgaagaaa aaacaagaa gaaaactgaa gaagaaaatg ctgcaagaaa aggagaagca   1800
ctacaagctt ttgaaaaatg gaaagagaaa aagatggaat atcttaaaga gaaaaataga   1860
aaggagagag aatatgaaag agcaaagaaa cagaaagagg aggaaactgt tgccgagaaa   1920
aagaaagata atttaactgc tgttgagaaa tggaatgaaa aaaggaagc tttttttcaag   1980 caaaagaaaa aagaaaaaat aaatgagaaa agaaaggaag aactgaaaag agctgagaaa   2040
aaagataaag ataaacaagc tattaatgaa tatgaaaaat ggctggaaaa taggaaaaa    2100 caagaaagaa ttgaacgaaa acagaagaaa cgtcattcct ttcttgaaag tgaggcactt   2160
cctccgtgga gccctccaag cagaactgtg ttcgcaaaag tgttttgata attctagttc   2220
ttacattatt tggttattta tcggtttgcc aatattagcc atagatttaa accattcaat   2280
tatttatagt tagaggaata tattttaatt aaatgccaga cactcctgct gacaatgaaa   2340
gaaatacttt ggaatgtaat cagtgaaagc atttttttga actgtagata aactgcctca   2400
aacaaagacc taataatcag attgttttta ccattaagat acataagatt ttatcatgtc   2460
ctgataattc ttatggtgga gtgattcatg atcttttttca ttaagctctg tatgttattt   2520
aagtatattt aattccagta ataaaaagga aatcatctag gtaccataaa aaaaa         2575
```

<210> SEQ ID NO 16
<211> LENGTH: 29750
<212> TYPE: DNA
<213> ORGANISM: Homo sapiens

<400> SEQUENCE: 16

```
tctgggtggg agttgggcgg gtcctgtctc ctaggcaaca gcacatgcac acaagcgacc      60
aataatgagc ccctctccaa agacccagga aggtgatgtc acttccttcg tctgggtggt     120
tgccccagcg acacgttggg ccgaagagcg gtgttgggta cccgagagac ccggcggtgg     180
ggaagtcact tcctcccgaa gacgctgttt cctagcaacc gccctccgcc tctgttatta     240
gcccctcctc ctcgctcggt ccaggaccgg ctctgcgggc gccgccaggc ccagaccaag     300
gtgagcagct cctacccgat gcttggctct tgattctcag ggtcgcggag aactggccgc     360
gggcgtccgg ggccgggaac agaaagcggg acctgggggc catgggggat ccggacagag     420
accgcgcttg gacgtgcacg ggcctggcgt tcgctggtgc tcagcatacg gcgcggtgag     480
gagcggcgag cacccggacg tcacctggcc tggtagggaa cggaacccgg ggcgcacaac     540
gctatgggcg gccctgccag gcctctgctc cgagtacggg aaaccgcgat tttaatgcgg     600
ctcatcgcga aagcttcgtc gttttgtctg gctctcttta acactttttgt gagaggaaaa     660
attggcttgc aatacatctc gctggctgtt tgcgggttag cattacgatc ttttttctttg     720
aatagcgctg tatgcaaata tatagataca ttttttttttt ggtggtggtg ctcataattt     780
ttacgccgac gatccttttg atggcctttt aaataagacg tgacttattt tgaaggcaat     840
gttatacttt agaagagagg tgaaaaataa ggtgttctat tttaattggc agcattttgt     900
cgtattaact tgtaatcatt tatttgcaga cttttttaagt agttgcaaaa ctatttttagg     960
ataacttcca tttgaatttt tttaaacaag cttgttatga aatttgcta tttcttttaca    1020
agaaccttttt taagtgaaga gtagcccaa tgttcatatc agatgctttt ctttgacctt    1080
tgtggggaga gtagaatcaa atgtaataaa ataaattctg aagcatgcga agtctgattt    1140
gttttgtata tttcagctac tatcagaagt tgaattctaa taattagcta ttttataaag    1200
gtaacgagaa aaaatacact atgtctgatg aagtttttag caccactttg gcatatacaa    1260
agagtccaaa agttaccaaa agaactactt tccaggtaaa gtattttttat ttggaatcat    1320
ttcacagtgt aaacactgta ttagatgggt tgaaattggt gattctagaa cagtcctata    1380
taaagcaggg gtaaatctta tattacttttt gaggttttgc acatgatcat gtttgggctc    1440
catccagtat tacaaactcc cctatatggt tttaagacta ccaaagtagc ctcaatacta    1500
gtttcctact aagttaaaag ttgaatcgca accttaaatt gccattttta tataaaaact    1560
tttttttctg ttgtaacata atgtttaagt ttttttttttct gttgagtcac tgcaattttg    1620
aactcagcct ctaagtttgc aatattgatt gcatccattt ctgaaatatg ccgagacaaa    1680
agctcttaaa ataccaatt tctttcaaaa taccagttttt taataaatta taatctaaat    1740
tgagccccttt cttatttgtt accctccagc tctaattata acctgcaatt aatttgttcc    1800
ataatgtgtg tctcctctag ttaaactgcg agctccatga ggaagggctc ttgtctgtga    1860
tgctctgcat tgagtatgag gcgtaaagtg ggtacatggc ataaagtgag cttgcaggaa    1920
atatttgtta gatgaatgaa acctaagttt gaaagcagtc gttaatcaag cattgtttgt    1980
ttaaagaatt acttgtgaat atgatacctc catgtttgga tggaaattga tttcagtatc    2040
tcatttcagg atgagctaat aagagcaatt acagctcgct cagccagaca aaggagttct    2100
gaatactcag atgactttga cagtgatgag attggtatgt gacagtatgg aaacgtgaac    2160
cacttttctt cttttttgctt ccttagttttt gtatttagcc agcccccccaa ccacccatcc    2220
cctcaatcac gtatgttaaa ataataccta agcattcact aattttagat tttcaacttt    2280
```

```
ttaattagta gaaagccact cttaattttc aggaagttgt atgattttct tttttattg      2340 ttgttttgtt ttctgaatgt gtatacgaaa atataaatta attgatggca ggtttgcagt      2400
aaaaggatgg ctgccagtgg taaaccacat tgaagaagac aggttcatct ttaagatcaa      2460
ccctaggagg tgctacagct agttagtaac tagtcccaca gaactaaact tcggtgcaca      2520
ttagaagtgc ttttataaag cttgctataa atcagatttt ttttggctgt gataaggggt      2580
aaatttaaaa accacagact cttcgtgttt catatatcag tactattata atttggtttc      2640
tcttagctat gtaaacatat taacatttta gtttcaggta taagcataca gaattctaaa      2700
cttggtgttt ttgtttgttt gttttgtttt ttgagatgga gtctcgctca gttgctcaag      2760
ctggagtgca gtggtgcaat ctcggctcac tgcaacctcc acctcccagg ttcaagtgat      2820
tctcctcctt cagcctcctg agtagctggg actacaggtg cccgccacca tgcccggcta      2880 attttgtat ttttagtaga gatggggttt caccacatcg gccaggctgg tctcgaactc      2940
ctgaccttgt gatccgcccg cctcagcctc ccaaagtgct gggattatag gtgtgagcca      3000
ccgcacccgg cctggtgttt tattctttaa aatttggtga ataattgtaa ttgatttctg      3060
taaaaccagt aataaccaca gttaaatcac tgctgtatag ttaacttagc atttcttatg      3120
attcttagta aatctaatat tctggtgtgg atggaattgt agttccaaaa ttttatgga      3180 aaaaatataa ttagtaatta ctaattaaat tcttccattt acaaatgttc ttgattttac      3240
atgaagaagt aatttgcaaa taaagtttt acagtccata atctaattta aatgctacat      3300
gactgattgt tagggacctt tggatggctt tttccagagc aaacagtgtt tggttgtttg      3360
gtaccctaca gacaacacaa taaatacatt ttgaataaat taatgaaatt ggaatttta      3420 tttcataaat gttaatgaga cgtgcctgag ttagctgtgt ttttagagct gcaagtctat      3480
ttataaaata catttgtgcc tattcattgt tagaattttg tttgtagctt ttaaggtaaa      3540
ctttgattaa gttaacgtaa ccttgacaat ttttaaaaat actgttgaaa cattttct      3600 tttccatttt tcagtttctt taggtgattt ttctgacact tcagcagatg aaaattcagt      3660 taataaaaa atgaatgact ttcatatatc agatgatgaa gaaagaatc cttcaaaact      3720 attgttttg aaaaccaata aatcaaacgg taacataacc aaagatgagc cagtgtgtgc      3780
catcaaaaat gaagaggaaa tggcacctga tgggtgtgaa gacattgttg taaaatcttt      3840
ctctgaatct caaaataagg atgaggaatt tgaaaagac aaaataaaaa tgaaacctaa      3900
acccagaatt ctttcaatta aaagcacatc ttcaggtaat tgttaggat tactgtaatt      3960 gcatttcttg gaagttatt ttaagataat cagtcccaaa atttttatat ggtagctagt      4020
atatatttaa gaaaaaaga cagacttaac ttccatttta cagacctgtt gtattttgtc      4080
taacttcaat tttacagacc tgttgtattt tgtctaactt caattttaca gacctgttgt      4140
attttgtctt gcatctaggc tgttgcctga tagaaagcca aagcacaaag ccaaagcacc      4200
tttagtcatc catagcatcc atagctgtgg atctccagac acctgacct gtgagcttca      4260 gttttgtttg taggtgtgga actggaatgg aatgctgtct aatccctctc acactccaaa      4320
gattagagtt acagcaatat tgagactaat ccttctaaca gtctttgcca taccaacatt      4380
gtgccagaaa atttcttga catttgtata tttgaaggat gagttatgtt attgctgctg      4440
ttgtttgttg aagcatccag gcactcctta agagaatctc catttgatct ctgtattgcc      4500
tatgaaaatc tactaagatt cagttttcca aggaaagtt cctggtgtga tctgggatta      4560
cagttagttc tgcccacaat tttactgaat tttaagcata aaggaacaaa gatagaatga      4620
aacggagacc aagtcctgtc acatacccctg ggccaccatt catgaacttg tatatgcaag      4680
```

```
gttaaggatt ttttgttttt cattctttgt attttataaa ggaattatta gttgatgtta      4740
accttcataa aaatctcctt gcatatcatc agtaaataca gtgctggtaa atatttcata      4800
ctttgcatat tagataccag tggtaacgtc agacaaaact ttatttcagg catgtattgg      4860
ggaactgctc ctttcttcct gaccccacaa tctcattaac tttgaaatga gcaaaggatg      4920
taagcagagc aaagaacact agaataatat ccaggacact gggggaaagg cctctgtata      4980
ttatatatga cttcagcaaa taagttaagc ttcagtatcc tcatgatgag gaagctaaaa      5040
ataaccctct ttctattcct gcaaaattgt gagagtttat tgaagtgcat ctcataaact      5100
ataaaaaact acaaaaatgc aaacagatgc ataatgaaac aattaacttg ttaaaatgta      5160
ccttctaagt atagtgagtg aaatcaatgc tggagagaag aggaacataa ttgaacttcg      5220
ttattaagaa aatgcgagca tatatagcaa ctaaaaattt gtctgagaca ggtggatgta      5280
tataattaga agtttatggt agataatcag gaaagcaata atccacctat ttcatacctt      5340
aaaaaaaaaa aaaacctgtg gtgggttaca atgaataaga aaatactgta ttttaaccac      5400
aaggtggcat caggatccta aatgctctac ttatatatgc aatgttatat tcagtacgtg      5460
taatataaaa ataattacct aaataggtaa ttgtatacat tgattaccaa aaaaagcgct      5520
tttcttaaag tataggcatt ttttttttctt tttgggaact tgacagtact tctggaagtg      5580 gaattttttgt agaaaatata ttaaagttgt cattctcagg ttcttcaggt tgaaaagtaa      5640
aaattgaggc tagtgttcct aagataatat ctggcatata taataagtat ttaaatgaat      5700
aaattaatat atgaatgatt tatctttgaa agagggaata tggttcatga gtttatcctc      5760 taaattctttt gacttttttt ttttctgtac aggtttggaa ctcaatgttt ttaatgtggt      5820
gagatattgc tgagtagcaa gtaatgcttt atgaaactat tagagcttga aggttttctc      5880
tgtccttgct tgtcttttgt aaaaagtata ataaccagac tttatagtca ctactgaagt      5940
gacagttgct ctataaagtg aaagtatttt tcacaggata tgttttttatt ttaatactaa      6000 catgactgaa atcatgaact ttggagtcag gatgcttctc ctttaatctg agatctgcag      6060
cctgctagag tttgtgactt tgggcatgag acctctttgt tctcatttta ttcatcttta      6120
aaaacgggat aatagttgcc tgcctctagg agtttgaggc aattaaatga gttcacatat      6180
ttgaagtgct tagaatagta ctggcataaa tttagcactc tataaatgtt ctgattattc      6240
attttattat ttagcgtttg tttataaaca tgctcagcag gtataaagta tcagtcatgc      6300
gggatgcgta agttctagag atctgctgta cattgtgcct atagttaaca gtactgtctt      6360
ttgcactgaa tgtattaaga aggtagatct catgtttgtt cttaccacaa taataaaaaa      6420
aattgactca acaccttctt tcaggcatta tataatattc tgcttaaact gaggctcaaa      6480
agacatgcaa gcatttgtca ggaggagaag caggaagtgg atattctagg caggggatc      6540 agcttaggta aagtatggt agcaggaggg attggaggga ttgtggtatg tgtgcatgac      6600
aactgttagc ccagcatttc agaaacacag atgacaaaat ggctgtagat aaggcagtga      6660
aggacaaaac cataaaatcc gttttatgtt gtttaaaggc agttaagctt ttattctgta      6720
ggattggatc atggggagcc attgaataat tttgtagaaa ggagtgatgt gatctgattt      6780
ggattttgta aatatcatgg aagcagtgat ctaggaaaga gtggataagg acccgacagc      6840
agggatgtag aaagtggaat aaatgagata tttggcaatt agaattgata ggatatattg      6900
atactctgga tttaggggat aatagaggga ggaatctaga gcccttggat ttggggttga      6960
acatttggct ggagtttagg atgtagctaa aattgtcagc tacttataat aataccaatt      7020
```

```
tggtatggtt gtggaatctt ctggcagaat ccataagccc attttaggt aaatgggagg    7080 aagatgttaa ttagaccaat tttgaagttg agaaaaatgc atttgtagaa caatagaaac    7140
ataaatatgt atagcaggta aaatgcaggc aaaaaatata tacatggaaa gtcttcccat    7200
tgtttcgaat actggatgca aatcagcatt tgattcttga tttaaactta gaagtaatgg    7260
aaagagtgaa attttaataa atgctaaaga agttttatgg actcagaaca attaactcat    7320
aaaagattcc ttcctctaat gagagttagc actcctatcc cttgagtgcc aacatcatca    7380
tctttgtcct tataatagca cttataatct tagtaatcta gtcttgtaat tttgtttaga    7440
aaaatcaacc tgtaaagtac ctggacaggt ccattgccgc tttgttgatt atgaggttta    7500
gtaacgtgta cagggcttgg tactcaaagg cttgatggat gagcctcctc attttatagt    7560
ggtagaaact gggggcaagat tttgttttgt tttttattt ttaacatttt ttttttaata    7620
ttataagagt tcacaatgtt gaagagttaa cttcttgtga ctggttactt tcaggatgac    7680
aactgtttct ttactttgtt ttttttttgt tgttgttgtt gtttggtttt tttttttttt    7740
ttagatggat ttttgctctt attacccagg ctggagtgca gtggtgtgat ctcgatctcg    7800
gctcactgca acctcagact cctgggttca agcaatcctc ctgcctcagt ctcctgagta    7860
gctgggatta caggcacgcg ctactaagcc cggctaattt ttttgtattt ttagtagaga    7920
cagggtttca ccgtgttagc caggctggtc tcgaactcct gacctcatga tctgcccacc    7980
tcggcctccc aacgtgctgg gattacaggc gtgagtcacc gctcccaaca tgtcgggatc    8040
acaggcgtga gccaccgcgt ccggcctgat tattaaccat catttatttg tgccttacta    8100
gagctctgta tagagaagag ttgtgggctt catctggact cttcaggaca gagaacaaag    8160
gggcataggc acaggaggga agtatggtag cacccagaga gatagataaa gccatggtca    8220 ttttttttata cacacacttt aagcatttta ttttcagca gaaaacaaca gccttgacac    8280
agatgatcac tttaaaccat cacctcggcc aaggagtatg ttgaaaaaga aaagtcacat    8340
ggaggagaag gatggactag aagataaaga aactgccctc agtgaagaat tggagttaca    8400
ttctgcacct tcttcccttc caacgccgaa tggcatacaa ttagaagctg agaaaaaagc    8460
attctctgaa aaccttgatc ctgaggttag cactaccact aaactgttga attgtgttct    8520
tgaatttatg cttttttatc tgattatgaa aaagagaagg agagaatgaa tttgtgtgcg    8580
tgtgtgtgtg ttttacatac tttcttctgc aactgataag gaaataattt ttaaaaatac    8640
actgtattcc accgagtcta aaactgcatc aattgtaaga cgtagcatta ttttacatac    8700
cactaaggaa gaaggaaatg catccaatta aactataaca caccagtgat tgtagagttt    8760
atccagtttt agagaaagta aaatgtcaaa aagtgttgct tttctgaatc tatataatag    8820
tgtttatctt taataatttt ttaaatttat gtatctttga attatgtaat ttatggctaa    8880
gaacaatata gtcagtgtca ttttatttat ttgattttat tcactcaaca aatgtgtgtt    8940
gaatgttcat ggcactcttc tgtgttcttt gggttatgtt ccaatagcat taaatgtggc    9000
ctttcaggtt tccatcaggg aatttactat gcattgttat taagggagaa cacttcgttt    9060
ttctctttgt atttcactat gagaagcaaa ctgtcccttc tgaacatttc agaagggaaa    9120
agtacaggaa gaacatttct tccccataat ctgcttgggc agattaggga actgcatgcc    9180
acctggccaa gcttctttct ttttctcatc gcttgtctgc agtgttggtg cttaaggatc    9240
tgctctctgg gaggtgaggc agaaggtgct gagaggagct cttttgtgca atgactaaat    9300
gggggaatcc ccctaattca gactggaagt attaggaagc acaataggct accaattcaa    9360
atcttgttct gcagttgagc tttaccagta aagctgacaa tttgatatac gcctaactga    9420
```

```
caccaccatg ctgtttctta atttgttctg aaaaccagaa gaagaaaccc aagcaaatac    9480
tttatattta agaaaattat ctgatccatt gaatattgtg ctagtttctt gtagctgctg    9540
taacaaattg ccacaaactg gttaacttaa aacaacagaa atgtattctc ttagttctgg    9600
aggtcagaag tccaagatca aggtgtttgc agggccattt tcctctgaag gcatcacgga    9660
agaatccttc cttgcctctt ccagcttctt tctagtggtt gccagcagtc catggcattc    9720
cttggcttgt agctggcttg tagctgcatc attcccttct ctgccttcat cccatgtggc    9780
cttcttccct gtgttttctc tgcatgtctg tgtctcttct ttctcttaaa aaaagacacc    9840
aggcattgga tttagggccc accctaattg agtgtgtcct catcttatct atttaaagct    9900
gtaaacacct tatttcctaa gaaagtcgta ttttgaggtt ctggatgaac atgaattttg    9960
gggcattaat gttcgtatgt taaacctagc attcccggga taaactctgg ttagtcatgg   10020
tgtgatattt tattgtggga tgtgatttgt taaaattgtg ttaaggtttg catctatatt   10080
tatgaagtct attggtctgt aatttttttc ttataatgtt accatcaggc ttgggtatca   10140
aatgagttgg ggagtgtctt ttcttcattt tataaaagtt tggtatcatt attttcttaa   10200
atgagaggat tcaccagtac aattatctgg gcctggaatt ttctgtgtgg agacatcttt   10260
ggcattacat ttgattttt aaataggtat ttcagtactc acattttctg ttttgccagt    10320
ttggtaattg tgtctatcaa gaagtttgtc catttcatct gatatgttga gtttataaac   10380
agagttgttc acgatagtcc ctcattcttt tgatgactag gattatcatg acatttcatt   10440
tttatttcta acatatataa tttgtgtttt gtgtctttcg tgctaaatct tgataggcat   10500
tgcttagttt tattaaacgt ttttaagaac cacttcggct ttgtcatatg ttggtgcaaa   10560
agtaattgca gttttggcca ttactttcaa tgacaaaaac cgcaatcatt ttgcaccaac   10620
ctaataattt tctctattgt ttgtttaatt gattttcagt attatttcag tattattcag   10680
tattatttct tttacttct ttttttttt ttgagacaga gtctcgttct atcgcccagg     10740
ctggagtgca gtggtgcaat cccagctcac tgcaagctct gcctcccagg ttcactccat   10800
tctcctgctt cagcctcccg agtagctggg actacaggca cccaccacca tgcctggcta   10860 attttgtat ttttagtaga cggggttt caccgcgtta gccaggatgg tctcgatctc       10920
ctgacatcgt gatccaccca cctcggcctc ccaaggtgtt gggattacag gcgtgagcca   10980
cggcgcctgg cctcttttac tttcttttgg tttaatttgc ttatctttag atttgaaaat   11040
tttctcattc attttaaga ttttcgtgat ttctgctaaa cctgttgaaa ggtgtaaact    11100
ttcttctttg tactgcttta gtggccccga tttttgatg cctttattt ttattatcat     11160 ttctttaaat atatatttta acttcccttg tgatctcctg ttttaaaaat ttattttttt   11220
agttgaaaaa taataattgt acatggggta catagtgatt tttcgataca tataatatat   11280
agtgatcatt gtgatctctt ttttgaccag ttggttattt tatggtgatt tattttattt   11340
tcaaatactt gttttttctc tagatatact tttgatgtta attataagtt aatttgttg    11400 tagtctagag aatgtatctt acatgatttc aaattttaa aaattattat tattatttct    11460
aaatggccca gctttagtgt atcttgtgaa agtctcattt gcatctgcaa agtagatgtg   11520
ttctccaggt gttgaatata atgttgtata atttaagttt ggtcaacatg gttggtaata   11580
tcattcagat cttctttatc cttactgatt tttcatccaa tttgtttacc cgttaccaac   11640
ttaggggtat taaatatcc agttatgttt gtgggtttgt ttatacttct ctttagttct   11700
gtcagtattt tataactttg ttatcaggca catacacatt tattattatt atgttttgag   11760
```

```
cattatgaaa cgtctctacc tctggtaata ttccttccct tatcttatag attgttttgt    11820
gtaatacttc agctttctta tgacaagtgt ttccatggta tatgctttct atcttttttc    11880
tttcaaacta attctgtctt ttcatgtaag tgaatctctt acaataagag tttggtgtca    11940
cttttttatt aagtctgaca atctatgcct tttaatgtag tgtttagtcc atttatgaat    12000
gttttgtcca tttaatgtaa atactgctat gattggattt aggagcaatt tgttgctctt    12060
tattttctat ttatctgttt tttaaaatta ttgttttat tgttgtttct ctgttactcc    12120
tttcttgcct tttttgagg agataatcat gaatctttta gttttttatt attattgacc    12180
ttttatctat atttgtttgc attgtatttc tcagagttga tcagtggatt acagaatata    12240
tctgaaaatt atcacaatct atttagaatt gatattgtat tgtttcacat ttgatctaga    12300
aaccttggaa taatatagtt ccatatactc cctcatccat tgtgctattg tcatatatta    12360
tatctacata tcctataatc cccacaatag agttataact ttttcttaaa gagccctttc    12420
agttttttgt attagacttt taaaaaatta aagaaggcta gaataaatat atattatata    12480
tctactgtat tatatattgt atatattata gataacattc tattgctaaa tatagataat    12540
atatatttgt agacaatatc tatatatagg taatatatat tctattctta tatattat    12600
agatatataa catctatata atctatttat agatattaca tatctataaa tacatataca    12660
atttctaggg atcttcattt cttcctgtag attcagatta ccattttgtg tcctgtcagt    12720
cttacaaact tattttacat ttcttgtaat acaggtttac tagtgatgga ttttttctcag   12780
tctttgcttt tctaaaagta tttgtctcat ctttgttttc aaatggtggt tgatgtgatt    12840
gtattcttct tgtctaacag ttgccttctt ctacctccag ctctttatag gtttccattt    12900
ttattggcct ctcttgtaat cattcatttc attgtcctct ctatataatg tgttgatttt    12960
gtctgaatgc tgtcaggaat tttactcaag attgtggttt ttatcttttg attacagcaa    13020
tttgactgca tggtgcctgg gtctagcttt ctttatgttt attctgcttg acgtttgttg    13080
agctttccaa acctataagc tgatactgtc tgtgaaatgg gaagattgtt atttcccacc    13140
ctattttca tcctctcctt ttggtactgt agttacacat gcattgaaat ttgtgctata    13200
tctcactgat ctctgagatt ctgtttatat ttcttaaatc ttttttcctc tttgttttta    13260
agattgaata acttgtatta cttagtcttc acgtttacag attgtggtcc ggagaatgta    13320
tcttttatga tttcaaattg tattaaatta ttttgttttg tttaatggcc ccagcaaaag    13380
ggtatgtcgt gagagttcca tttgcagttg caaagtatgt gtgttttcca ggtgaatttt    13440
ttatttcact tattgtggtg ttcaacttca gatttctat tggtattttt tctgtttttt    13500
aatataaaat cccccatctt ttcagccatc atgcatatat tttccccaaa gtgcttgaac    13560
atatttatat tagctatttt aaagtccttg tctgctaact ctaaaacgtg agtcatctct    13620
gggttggttc ctattgacca ttctctgttt ttttattttg tttttttaaat aagtgtcacc    13680
attttctgtt tctttagtga cttttgattg aataccgggt gttctgaatg atatttttgta    13740
gagattctgt attcttttat gtcccttcaa acatattttc tagcaagtgg atatcatggc    13800
tggacacaaa ttcccaatcc tgtttctcct gcagtggata tcagctgaaa tttctgctta    13860
attctttca gtttctagct tctatgcttt tacaggatcc tctgaggtct cccttatgcc    13920
acaaatagag gtggtaaagg ttttttggtga atttcatatg cagattttgt ggtcactgtc    13980
ctctgctatt ttccacatac ttattggctg atctgatggt cctagactca gtccctgtt    14040
ccctcaagtc attccaccaa ggctgtagcc ttcattact tgagctgcat agactggaga    14100
atgccttctg gcaaaaagct actaatttgc agatctcctc aggtgaagct ttatctttca    14160
```

```
gggtagactc cagtgtctca gcacttcttc cattttctca aatgttttct ctccattgct   14220
tttgacatat aatttccttt gcacccataa aatactgcgg agaaagaaaa ttaaagtatt   14280
tgtacaacaa agttgaactt cctacattgt aatatcatta cctttaggct agatgattct   14340
atgaagaaat gtttacctta gatagacaaa tataattatt tcatatcaga tagaattttc   14400
agaattttga ggaaaactca agtgcatgca atctatgtgc ttttcctatc taaaatattt   14460
ggaagtagcg gcttacttga ttttattaaa tgctttcatt tggataacta gtaatatttg   14520
cttggaacta agtatttta cctgtcttct ttatgctttc cttcaaagga taattgtagg   14580
aagagctatc aaaatcaaat cttggcctta aatatttata agaaatgtga ttattaagta   14640
ataggagttt tgaaaattgg taaaaaataa atagagaggt ggtggtagtt aaagaacttg   14700
aataactctt tcagtgaccc cttttaatga ccaagacatc aaggcttgaa agtaaagcat   14760
gcttacctcc attggcttgt cacactttgc gtttcagcaa caaatgccta ataatgcag    14820 atttcagagt tatgcactat ttcaatttgt agttttaata atgctattgt tcccataaat   14880
gttaattatt aaacttatgt ggcaaatgta tttttttttg cgaaaacagg attcatgctt   14940
aacaagtcta gcatcatcat cacttaaaca aattcttgga gattcttttt caccaggatc   15000
tgagggaaac gcatctggaa aaggtggtta tatctaataa ttatatctta tatgtgaact   15060
ctgtactact tagactcctg tttgtaagag aaataatact ttgtatagtt ataagagaaa   15120
tatatgtttt tatgtgtttg agttttaatc ctgactatgt agttaactaa ctgtgatttt   15180
ggatgcagaa cttaatctct cagtgcctca atttccctaa gttatattat ttgtctcata   15240
aggttattgt gaaaattaag tgatatagtg cattttagcc attagcctag ttaatagccc   15300
aagtggagtg agcacttaag gtaaactact gttatgtatg tgttgctgtg atattctgca   15360
ggacaacata atagctaggt ggaattttaa agtgagacta agctagattc caatacaggc   15420
acaattacat aagcaaagta actaaccttt ctgaccctgt atgttgatct ttaaaatggg   15480
taaaataaga gtaatttgcc ttatagggtg ttgtaagaat taaacatgta aagcatttac   15540
agcaatacca tagtaagcac ttggtgtgat atgtgaattg ttaacataat ttcttttctt   15600
agtgatacgt agcttaatga aacctaaaag acatagctat ttctaggtct gagatgtgta   15660
atgaacattt tagtgcttac tatgtagtat cattttgtc attttacaga tgagaaaagc    15720
tgaagtgcag tgacttaggg aaacataccc aaggtcagtg atggaaccat agttaaatct   15780
tgagttccaa agttcttgtt cttttcactg aacagattaa cagctccaaa gaatccaata   15840
gtgaattgag tgattttaag cccatgttac ctcaaaacaa attccaaaaa aatggtcata   15900
atgaaaccaa cagaattaag acttttcaca gtaaagattc aggtttagct gcaaggtgga   15960
cgttggtaga actgaaagtt ggtgatccca ttccaaaatg tggtaaaatc agaatagtag   16020
aagcaattct ataaatgcaa aactgaatct tcttatgcca gagcttgagc ctgtttcttg   16080
gagcactgag aggataagca ataggcttgt ctttattgcc ccttatggta tcagaggaag   16140
tactacatct tggtgagatg aaactcacta gagactgtgt aaaattgcat taattcttgg   16200
ttctttctgc agctatacaa ttcaacaatt gtactactag taactgtagt agcctagaga   16260
ggtgtgacac cttcttatgc agcgtgttgt tccagctaag aaactcaggc tttagagtta   16320
aacaaatatt gtcatctcac ttacttggtt tgtatatcaa caagctcttt tgacatgtcg   16380
ttgttttagg gtagttattc cattctgttt attaatatgc tattttttcta agtactagat   16440 ttgttaagtg cttcattagt taagcctaga ctatttttt ttgtaaatca ctttcgaaaa    16500
```

```
gagtttatgc aagtttaata tgataacttt tcttcatatt ttgcaagaaa aaagagttta   16560
tagatagtcc tcatttaaaa gaaagcaaat gaatcaagta tttaccttat taattcagaa   16620
gggggtttta atgctattac tctgtctcaa aatagatcca aatgaagaaa tcactgaaaa   16680
ccataattcc ttgaaatcag atgaaaataa agagaattca ttttcagcag accatgtgac   16740
tactgcagtt gagaaatcca aggaaagtca agtgactgct gatgaccttg aagaagaaaa   16800
ggcaaaagcg gaactgatta tggatgatga cagaacagtt gatccactac tatctaaatc   16860
tcagagtatc ttaatatcta ccagtgcaac agcatcttca aaggtatttg taaaaattca   16920 tactttcat actacagctt aaaacttgaa atagaacttt aagaaatttt atcttctgtg     16980
ttatatactt ctgaattacc agtggaaaat ttatcttttg atagtgatat tgtattgtca   17040
catggttctt acttaatcca ataaaattta actttaagga aagtttgtag tgaatataat   17100
gaaacccagt gtttaaaaat tatcagaggt gtgtgatcat aatatacttt taaatgtctc   17160
agaaatgcat actcatagtg tatatatttc cataggtctt catatttta aaatataact     17220 gtctggaata atttctgaga ttttaaatta gagttatgtt tttggatatt gttttaaaac   17280
gtgttaacaa ttttaacaaa aatcttaaag aaatgtttat caacagttta tcaacatctg   17340
tgcttcttta aaatagatgg ttatcatcag gaacattagt attattattc gtatttgatc   17400
ctttgccttt atttcctaat tttcaaaata atgaactggg ccctggcaa cctccagagg     17460 tgatgaagtt gctttgtttt ttcttttttc aattcatgta aatttaatgg ttacaagtgc   17520
ttttttgtta catggatata ttgtgtagtg gtaaagtcag acttttagta taaactaaaa   17580
tgtacattgt acccattaag taatttctca tcccgcacct ccctctcacc tttcctagtc   17640
tccattatct attattccat accctatata catgtgtaca cattatttag ctctgacttg   17700
taagtgagaa catgtaccat ttgactttct gtttctgatt tatttcactt aaggtaatag   17760
cctccagttc catccatgtt gtaaaagata ttatttcttt tctgtgtggc tgaatagtat   17820
tcctgtgtgt gtgtgtgtgt gtgtgtgtgt gtgtgtgtgt atacacattt tctttataca   17880
atcatatgtt gatgtacact taggttgatt ccatatcttt gctattgtga ctagtggtgt   17940
gataaacatg agtgcaggta tcttttttat ataatgattt attttccttt tggcagatac   18000
tcacagtggg gttgctggat tgagtggtag ttctatattt agttccttaa gaaatcccca   18060
aactattttc cataaagatt gtactaattt acattcttac caagagtata caagcattcc   18120
cttttctctg tgttctcacc aacatctgtt actttttta ctttttaata atagctaaat     18180
attctgacta gtataatata tctcactgtg gttttaattt gtgtttctct gatgattagt   18240
gatggtgaac attttttttc atgtttcttg gccacttgta tgtcttcttt tcaaaaagtc   18300
tattcatgtt ttttgccctc tttttagtgg ggttatttgt tttttgttgt tgttgttgag   18360
gggaacatta ttattataac cttaagaaac agatatgtaa tatgtaggat tacttgtccc   18420
tacattaaat tgtgcctgag tgctatactt taaaaattta tggtgtagca ttttcagtct   18480
ttgtttctcc tgaatttgtc attatctctt gtagctgcaa ttagctagca gctctgtgtg   18540
tttattatca gcggaagaaa acagggctag ctgaaaattt gtgtttgagc aatacttta     18600 taacataaaa tacaagcttt tcttaaaatt gatgaaggag gttcattaag ccatgttcca   18660
ggtatatcat ccttagctaa tttctttagg aaaaaaacac tactgctaag ttagggatgt   18720
gtttattatg tctgtgctct cactttacca ctagcaccca tcagtctgtg taaagtagaa   18780
aagttgttcc ttaaaagaag aaaggatatt ccggagttta tagacaggat tgtagaatgt   18840
ctaatagagg caattctaaa ttagaacagg catttcatat gtaacaagta aggttgtaac   18900
```

```
ttgtttcttt tgactggacc cttggcctca ttcttactct ctactgaatg acctttttcta    18960 aacagaaata taatcattct ccattaaagt cttttttgttg gtttctcatc acaagaattc    19020
catccagact cctcatcgct gcctagtgat ctcacctggt tcttccctga ccacgtcttc    19080
ctccgctttc cctgccattc actatgcttc agctccattc acctctttct gttttttcaga    19140 gataacaggt tccgtcccttt tcaggctttt tacccacttg ctgtttcttt ctttcataga    19200
cctttcggtg ggccctttgc actcttagct ctgatgtcag cccctcagga cagccttccc    19260
tgaccaactt ctttaaagca gctcctcagc cccactctag tcattctctg tcactgcaca    19320
ctattttatg tccttcatga gccatgtttg cttatatatt tattttttggt catccgtctc    19380 tagaatttaa tattcttaag ggcatttttat tcactgattt gctcccaatt tctactgtgt    19440
ttgacacata gtagatgctt aaagaatagt gatttactgg cagtttggct tctaagccta    19500
aaaaggatag ttgtcatgaa taaatcatct ttggcattttt ctgtttaata gaaaacaatt    19560
gaagatagaa atataaagaa taaaaagtca acaaataata gagcatccag tgcatctgcc    19620
aggtaataaa gttaccaata tttgtcattt atgggcttgc attctagcaa agctagtttt    19680
aatttaactt tcataaagta aatttcattt ggtgttactg tattttctttt ttatttccat    19740 ttcataaaat gaaagtagtt aacttcatga taaaacccct tggttgatga tattatttga    19800
aataaagtaa tttataaaaa gtaagtctat tactgattgt tttagtgcct ggaatgttta    19860
tgcaatacct ttgctctcca ggatcgtcct aggaatattt ttcttctttc ttaatgtcag    19920
tgattaggga ttctttgtgc tccagactgc ttctggaata gagcttcttt ctcctacttt    19980
tcctgagaca agcaatataa aatggtaata aagctgaagt ctagcaatga tacttattca    20040
ttatcaagta tcattgtcta acatgagaaa ttgtactgaa agccttcaga atctatgaac    20100
taagtaggtt tattaaaatg attatctgta tagcttcatt cacaccaatg ataatgaatg    20160
cctaactcat aagtgctaat caaaaacctt ctgaatcttt aaaattatcg ttagtcaaat    20220
tatcattaat caaataaaac agagctagca agcttttttct gtaaatggcc agttagtgca    20280
tattttaggc tttgtaggcg atacagtctg tattggaact actcatttct gctattttaa    20340
caggaaagca gccacaggca aaacttaaca tgaatgatta cagctatggt gcaataaact    20400
ttgtatatca aaaccaatgg ctggccaaat tttcccacca atccctgata tagatagtac    20460
tattctttct aattttatat ttggaatgct tcatgtaaca aaatgatgaa agaaaatatt    20520
aaaagagtga ttataaccta ctgtattgtt ttttccatgt aacttgagaa gtggtccata    20580
tttcttaagt ttcaattac aaatatttaa aaagagcaat cattttaaag ctatataact    20640
taaagttata aaatttaaat tatgttgaag gggacatatt taagttatgt ccccttctac    20700
ataatttaat attctttgta tactaagact gtacattttta cctacatcat tttcaaagta    20760
attataattt gttaaattat aatgtagttt ccaatttttt ttttgagatg gagtctcact    20820
ctgttgctca ggctggagtt cagtggcatg atctctgctc actgcaacct ctgcctcctg    20880
ggctcaagct atcctcccac ctcagcctcc agggtagcta tgactacagg catgtgccac    20940
cacgccagct aatttttttgt attttttggta gagacagggt ttcaccatgt tgcccaggct    21000
ggtcaacagc ccaacaggat gagctcaagt catccaccca ctttggcctt ccaaagtgct    21060
gggattacag gtgtgagcca tcatgcctgg ccagttttca aatattatac gtgcatattc    21120
taacagatct ctcttctacc aaatgcaatt gtaatttttt gtcttgattc atttggatct    21180
tttcagatta atgacctctg agtttttgaa gaaatctagt tctaaaagga gaactccatc    21240
```

```
gacaactacc tcttctcact atttagggac tttaaaagtc ttggaccaaa aaccttcaca   21300
gaaacagagc atagaacctg atagagcaga taacataagg gcagctgttt atcaggtaaa   21360
aaaggaaaat attttttaaga gaagaagaat gatcactttc ataagcctac actgtttata   21420
aagaataaag taatcctgat agaaaatgat ggtttaatac ttaaatttat tgagaaagag   21480 tttccttttta atacatgagt aatcatattt tactaaatta tttgcttcca cactttgcat   21540
aactgaccat agttgttttt aaagaaagaa tatgccattg caatttatag aaatacagca   21600
caagccaaaa cattgtaaag tctatatatg ttttcatttt tttcttcttg aagtttatat   21660
gaacaaaagg agttattatg aacaaaaagt tattaaattt tttctttcct gagatgttgt   21720
taggcgtaca taggaaaaag attgtattaa tttattcaca attctaaaag tcttttttttg   21780 tcttttttag agtagaatag tatacttttag aaaattgtac atgtgaattt cagagaaaat   21840
gttaatataa agaattctaa ttcacttaag aaattttaaa tattatatga ccttttttctt   21900 gttcttatag gagtggttag aaaagaaaaa tgtgtattta catgaaatgc acagaataaa   21960
aagaattgaa agtgaaaact taaggatcca aaatgaacag gtattctgac atatagaagt   22020
aaaaatgttt tggatttttta tttcagtaaa atatccctga atatataact tttctaaatc   22080 agcttttttaa atggcaaaat aacttgtata ttaaagaaat gatttccggt tttacttctg   22140
ttttacttta tacattttag tttgatataa ctgttttaca tgaaaacaga ttttaatttt   22200
gtatatgtat aggatagctt tgttcctgct gattatgaag ttattattgt ttatgagcac   22260
ctaattcact tttaaaagtt gatttcattt agaacttaac caagaaggcc aggtactgtg   22320
gctcatgcct gtaatcccag cactttggga ggccaaggca gatgggattc cttgaggtct   22380
ggagttcgac accagcctgg gcaatgtggt gaaacccccat ctctactaaa aatacaaaaa   22440
ttagccaggg atggtggtgg gcacctgtaa tcccagctac tcaggaggct gaggtggcag   22500
gatcacttga acccgggagg cggaggttgc agttagctga gatcgtgcca ctgtactcca   22560
gcctaggtga cagagactct gtctcaaaaa aaaaaaaaaa ggcacgacaa gataaaggat   22620
cattagacac tagttagcct tcaatttttcc tctttttctct cttgaatttt ataagtatct   22680
tcaagtccaa cccctacctg aactcttgat ctgtatcctt tcccattgaa tggaggtgaa   22740
cttttgttcc tgtctcttct gtactgagtc tcttcctcta actcctgctt gtaatacgct   22800
cagttatttc ttatcttcta aagtcaaact tctggacaaa aactccagtg tgctgttcaa   22860
tactaaaaat agatttagaa gaaaatatat ttccaaggtg aactgcacga taatgcgtca   22920
gtagtgaagg gagcagccct ccaggggggcg tgcctgtcta tctgttaacc acgttcatag   22980
cagtatgctg ctgtggtcag tgccatacccc cttctcattt gatttttcgta gctctgtgag   23040 gtagatagta ctttgacctc taaattatgt taccccaata ttaaggtttt atgtcattta   23100
atattgaaca ataaagcaaa catagaatat tatgggatta gattgaagga agtaaaataa   23160
taacataact tgctatacag tctccaacct attttttcagt cgagcacata ctttcaacat   23220
ttggaataca tttgtgcagt aagaacttta tgttttgata ctattcaaaa ttaagattta   23280
aaccaaaaat ctgcatctta ctgcatggct tggccaattt gccttactct aacttacttt   23340
ataagcccat aacttttactg attttttttttt caaatatttt attatgaaaa ttttactata   23400
ccacttagcc tattacagtt tatttttgata taattttgttt agtacacttt caaaaataat   23460
agttgacatc tttctcatta ataggtcaat atgtgataaa tgttttttaga aaggacgtt   23520 ttaaaaccaa tgaataattc agataacatt ctttgtaaat tatctaagcc attctaaata   23580
aattacctac tttgaaagtt aatttctaag tataatgaat atcagaggac taaagataaa   23640
```

-continued

```
tgtatatgtg tatatttata tctagccata tttgtgtcta tgtatatata catatatatg   23700
tatatcactc tattatttt tccactgtag aaaaaagctg ctaaaagaga agaagcatta     23760
gcatcatttg aggcctggaa ggctatgaaa gaaaaggaag caagaaaat agctgccaaa   23820 aagaggcttg aagaaaaaaa caagaagaaa actgaagaag aaaatgctgc agaaaagga    23880 gaagcactac aagtattcag aactttgcac atcttaatta ttttaaaaca tttgaaatcc    23940
aaattaatga ttaaccatat ttttatttat tttcaaatat tcacagtaag aaaattattc    24000 tgaactttt caggcttttg aaaatggaa agagaaaaag atggaatatc ttaaagagaa     24060
aaatagaaag gagagagaat atgaaagagc aaagaaacag aaagaggagg aaactgttgc   24120
cgagaaaaag aaagataatt taactgctgt tgagaaatgg taatccaaaa tcataaaatat   24180 tttgatatat tttaaattat agtaacactt caggatttta taaaatttat ttacttgaaa    24240
tttagtaatg catttcaatt tcattactgt caaagatgta ctagggaatc tttattatgt    24300
attttccttt aactctccag tgttttatac tatgctctat aggaatgaaa aaaaggaagc     24360
ttttttcaag caaaggaaa aagaaaaaat aaatgagaaa agaaaggaag aactgaaaag     24420
agctgagaaa aaagataaag ataaacaagc tattaatgaa tatgaaaaat ggctggtagg   24480
tattatttgt caatgcactt tcgtcttttt catgtaccttt ttgtgtcttt tctgtcccta     24540
attctaattc tatttgctcc agacctactg atcatttcta cctggaatct gctttgttga    24600
attcaagctc tcctcctgca tatagcatat tttctttgac ttagtcattt ctattaatgt    24660
ttctactatt ccctcaaaca cccaggctga aaacttgtta taatcttctt ccttacctgc    24720
atccccacat ttaccattta ctattcatgc ccattcttcc tttgctgtga ttctcacatc    24780
taacatagaa agaagacaag tttactattg agggtactac gtggtggaac ttggtcatga   24840
caaaaagtaa cactgaactt aatagtgaga aaattattcc atctttatt ctcttttgat     24900 gtttctgatg acctcaagga gaatctctta tttaggaatt tttaatgaaa gagagcaggt    24960
ttgaggttta ggaggagcaa tagctagctg aaccagatat gtgtatatat ttgatttcac    25020
tttacttatc tttataaaag ttactttttg ttgatgtcaa gcaaaatatt attttccatt    25080
ttagaatatc aatataaata tgcattttgt ccatgtttat ataagtaata cattactatg    25140
aataaatact ttcataagt aggtaacaca ttcatatgaa tagttaacat attcatatga    25200
ttcagcaacc aaaattatag tatttttgca ctagaagtct atccagtcag gtttcctatc    25260
aaactttaaa acaactcata ccaatcaact aaatcatcca ggttgttttt gatttgcatt    25320
tctctggtta gaattgagct tgaatatctt ttcatttgta tacaggccat ttatctatta    25380
ttttctctgt aaattgtcat ttcatagact ttgcacactt ttctattaga ttgttggttt   25440
ttttccttta ctggtttcta gaatcttttg ttttgtactg gggaaattag cctatcattt    25500
tttatatggg ttgcaaatat ttaccccac tatattgttg gtttcccggc tttccttata    25560
gtatctcatg ccatgaagaa tttaaatttt aggtgtcaga tttctgtttt ttttttttgg    25620 cttttgatttt tcaagcatag ttgaaaagac ctacacaatt tgagattaaa cagaattatc   25680 ttattttct tctaacaact ttgtgacttt aatatcttaa tgttttaaca tttgttctgc     25740
ttggaatttg ccctgataca tggtgggaaa tatgatttca actttagttt ttccaaatgt   25800
atcctttata aagtagccca ttttttaccca ttgatttgag gtgctacttc tgttatatga   25860
taccttctca tgttttcggg tctgtttctt aactttctgt tccattggtc agtctcgtga   25920
ttccagtgcc acacttccat tattaggctt gatatgtcta aatatctgct tggattcatc   25980
```

```
tcctttata gttcttcttt cacagtctttt ctgaccagtc ttgtttattt attttttcca    26040
taaacttaag aatcagcagt agttagaaag gtacatggga ccaaaatgag cgatttaaag    26100
ataggataaa aagataaaac aataataaac ttaagaaaca tgccagacca acataaagaa    26160
aattgtagaa ctctcctgaa caacacaaat gaagacttga gaaaatggat cagaattgcc    26220
catgcacaga aacacactta accttataat gatgttataa ggatgtcagc tctccctgaa    26280
gtcatttaat gcaatcttaa caaaagccaa caggattac tctgtgtgtt gagtttagta     26340
ctgctatatg ctaattcgat gcagagaaat agtaataaaa taaggtaatc aaaattggtt    26400
caattttgaa tgaaaaggt agtgtttcat gatgatttcc ttaagttaat ctgttaaata     26460
atgctatgtt ctaaaaaaa atttaaagtc cacttatatt aagaagatgt acactgactg     26520
ctagtatcaa ttagggaaat taaatgtaaa catttgagtt ttccatttta attccatatc    26580
ttcatgaaaa tggaatagaa tttctttaat aagtcacatt taggtatact gttttaatt    26640 atagcactta attacattgt cattcttatc agtcctctga agaacaagaa ttcctcaaag    26700
accaaagaca aaataacatg tttgatatct agtaaaatgt ctgcaaatat agtacaccta    26760
taaacacata aacatacatg ttacagatcg gttctccttc ttaccaaatt cttattgaaa    26820
tttgtttgca gatagaatag aaaaattgcc cctgtatagg agtctaatga cttcagtttt    26880
catggaaaac aacatctcaa gcttttata tacaaactag tttgaacagt aagcatttgg     26940
tgggtaattg cttagggga aagttaatag ccaaagatca ggtaagacta aatatttt      27000 cttgccaatt accagattaa ttcatcatta cctttagtaa gaaaataagc aaaaagctca    27060
gttttccaca aataaatgtc tgaaggactt tttaacaagg ttcttttaat tactatcaag    27120
gtgactattg attcttttga actgatatta cagttaatat aattgtctat ttgctaccct    27180
ggctttacag ctccctgcta gtaagatgaa gcatatttca agttactgcc ccctcatgtt    27240
aagtgaaatt acaaaaagag atttattcag tcaatttctg tggacacagt ctggtcactg    27300
cttttcttcc gcctagctag atggtctgtc tctaaaatat taaaatgatt gaagatgatc    27360
taattacagc tttgcttttc tcaattaaaa ttctgaaagg aagtttcctc tttgccttat    27420
tagaaatagc aagcaaacaa acatgcaagc attcttatga catggaatga ggatatgggt    27480
gttaacattg acaaaaaaca aacaaacctc ccacttcact tgtttgtta catgtgaatg     27540 gaaagcttgt cctgtattgc catattattc ttgtggcatt tatatatata ctgatgaaaa    27600
gatgcataca tacctaatca tttttccataa tgcctttcct cccaagccat caacctgcag    27660
aggcaggttt cactaagggt tttcctgctc cttgaggaat atgagaaaaa taccaagatg    27720
aagaaaccac caaaccttat agtgttagca gagacataaa gggacacctg gtgcccctct    27780
tccatttctt gtctcctgcc ttctgccaag ccttagtcac aatggatatt tttgtttcct    27840
cccacagcac acattttttt tcccactctc agagccctca ccactactgt ttgcaagcaa    27900
agctcttccc cgatatttat cacgagtggc ttctcttatc catcatgtca cacttcaaag    27960
ggactttccc tgagtccatt ttttgttgaa agtaaatact ctttttatt ccttctcata     28020 gttttaaaac atgtttcaga gaaattcaca caatttggaa ttatctgttg tttattttct    28080
ttgtttctgt ccattttgaa agttccctgg gggacaggga ccatatctgt gtgttgggat    28140
tttaaaaaat tattttttatt tgcaaatgac acataaaaag tgcacatatt tatggaatac    28200
agtgtgatgt ttccatctac attgtataca ttgtgtaaca atcagaaatg actcacaaag    28260
gtaggcaaaa tgtttgatgc aaagatatca ttaatattta ttataggaaa gtacacaaat    28320
tactaaaaat taaaggcaaa taccatacat ttaaatgggc caaataattg agcagaaaat    28380
```

```
ttacaaaagg ctaaagaaat gtttgaaaat gtgctcaagt tcaataataa agaaacatga    28440
ggcagaattt ttaactattt gtaaaaaatt tgaagtatct catactgtca tgacatattg    28500
aaactttgca cccagtaaac ttacttctga gaatttgttc tcacgaagtc accaccaact    28560
tataacagtt actatatttg agttataatt ataggtcttt ttttctattt tatacaattc    28620 tttttaatg ttttcacttt taaagtttaa aaaattaagt gatattagta cttgcaaatt    28680
gacaatgttt actaatttt tcttgtttc cattttttgt ttgtttgttt ttttgagaca    28740
gggtctcact ctgttgccca ggctggagtg cagtggtgca atctcggctc actgcaacct    28800
ccacctccca ggctcaagca atcctcccat ctcagcctcc taagtaggtg ggactatagg    28860
catgcaccgc cacacctggc taattttgt gttgttttgt agagatgatg tttcaccatg    28920
tttcccaggc tggtctcgaa ctcccaggct caaacaatcc acccaccttg gtctcctaaa    28980
gttctgggat tactggcatg agccaccatg cctggcccta cctgttattt ctttatgatc    29040
tgttaaacta ggaagtgata tataaatatc ctataatgga ttattttgtt cttcagcaag    29100
caacctgatt tgaaaataat aatcatatat gtacataaat ttatagtgtt ctattttctc    29160
tttaggaaaa taaggaaaaa caagaaagaa ttgaacgaaa acagaagaaa cgtcattcct    29220
ttcttgaaag tgaggcactt cctccgtgga gccctccaag cagaactgtg ttcgcaaaag    29280
tgttttgata attctagttc ttacattatt tggttattta tcggtttgcc aatattagcc    29340
atagatttaa aaccattcaa ttatttatag ttagaggaat atattttaat taaatgccag    29400
acactcctgc tgacaatgaa agaaatactt tggaatgtaa tcagtgaaag catttttttg    29460
aactgtagat aaactgcctc aaacaaagac ctaataatca gattgttttt accattaaga    29520
tacataagat tttatcatgt cctgataatt cttatggtgg agtgattcat gatctttttc    29580
attaagctct gtatgttatt taagtatatt taattccagt aataaaaagg aaatcatcta    29640
ggtaccataa tgatagaaat tattcctttt gtggatgatt gtgaatctag attcaggttt    29700
ttaaatgaag ggtcgctggg aagtgcgcat atattattcc ttctgaaact             29750

<210> SEQ ID NO 17
<211> LENGTH: 200
<212> TYPE: DNA
<213> ORGANISM: Homo sapiens

<400> SEQUENCE: 17
acttccttcg tctgggtggt tgccccagcg acacgttggg ccgaagagcg gtgttgggta     60
cccgagagac ccggcggtgg ggaagtcact tcctcccgaa gacgctgttt cctagcaacc    120
gccctccgcc tctgttatta gccctcctc ctcgctcggt ccaggaccgg ctctgcgggc    180
gccgccaggc ccagaccaag                                                200

<210> SEQ ID NO 18
<211> LENGTH: 139
<212> TYPE: DNA
<213> ORGANISM: Homo sapiens

<400> SEQUENCE: 18
ctactatcag aagttgaatt ctaataatta gctattttat aaaggtaacg agaaaaaata     60
cactatgtct gatgaagttt ttagcaccac tttggcatat acaaagagtc caaagttac    120 caaaagaact actttccag                                                 139

<210> SEQ ID NO 19
```

```
<211> LENGTH: 85
<212> TYPE: DNA
<213> ORGANISM: Homo sapiens

<400> SEQUENCE: 19
gatgagctaa taagagcaat tacagctcgc tcagccagac aaaggagttc tgaatactca    60
gatgactttg acagtgatga gattg                                         85

<210> SEQ ID NO 20
<211> LENGTH: 321
<212> TYPE: DNA
<213> ORGANISM: Homo sapiens

<400> SEQUENCE: 20
tttctttagg tgattttct gacacttcag cagatgaaaa ttcagttaat aaaaaaatga    60
atgactttca tatatcagat gatgaagaaa agaatccttc aaaactattg ttttttgaaaa  120 ccaataaatc aaacggtaac ataaccaaag atgagccagt gtgtgccatc aaaaatgaag   180
aggaaatggc acctgatggg tgtgaagaca ttgttgtaaa atctttctct gaatctcaaa   240
ataaggatga ggaatttgaa aaagacaaaa taaaaatgaa acctaaaccc agaattcttt   300
caattaaaag cacatcttca g                                             321

<210> SEQ ID NO 21
<211> LENGTH: 227
<212> TYPE: DNA
<213> ORGANISM: Homo sapiens

<400> SEQUENCE: 21
cagaaaacaa cagccttgac acagatgatc actttaaacc atcacctcgg ccaaggagta    60
tgttgaaaaa gaaaagtcac atggaggaga aggatggact agaagataaa gaaactgccc   120
tcagtgaaga attggagtta cattctgcac cttcttccct tccaacgccg aatggcatac   180
aattagaagc tgagaaaaaa gcattctctg aaaaccttga tcctgag                 227

<210> SEQ ID NO 22
<211> LENGTH: 94
<212> TYPE: DNA
<213> ORGANISM: Homo sapiens

<400> SEQUENCE: 22
gattcatgct taacaagtct agcatcatca tcacttaaac aaattcttgg agattctttt    60
tcaccaggat ctgagggaaa cgcatctgga aaag                               94

<210> SEQ ID NO 23
<211> LENGTH: 248
<212> TYPE: DNA
<213> ORGANISM: Homo sapiens

<400> SEQUENCE: 23
atccaaatga agaaatcact gaaaaccata attccttgaa atcagatgaa aataaagaga    60
attcattttc agcagaccat gtgactactg cagttgagaa atccaaggaa agtcaagtga   120
ctgctgatga ccttgaagaa gaaaaggcaa agcggaact gattatggat gatgacagaa    180
cagttgatcc actactatct aaatctcaga gtatcttaat atctaccagt gcaacagcat   240
cttcaaag                                                            248

<210> SEQ ID NO 24
<211> LENGTH: 71
```

```
<212> TYPE: DNA
<213> ORGANISM: Homo sapiens

<400> SEQUENCE: 24
aaaacaattg aagatagaaa tataaagaat aaaaagtcaa caaataatag agcatccagt      60
gcatctgcca g                                                          71

<210> SEQ ID NO 25
<211> LENGTH: 169
<212> TYPE: DNA
<213> ORGANISM: Homo sapiens

<400> SEQUENCE: 25
attaatgacc tctgagtttt tgaagaaatc tagttctaaa aggagaactc catcgacaac      60
tacctcttct cactatttag ggactttaaa agtcttggac caaaaacctt cacagaaaca     120
gagcatagaa cctgatagag cagataacat aagggcagct gtttatcag                169

<210> SEQ ID NO 26
<211> LENGTH: 90
<212> TYPE: DNA
<213> ORGANISM: Homo sapiens

<400> SEQUENCE: 26
gagtggttag aaaagaaaaa tgtgtattta catgaaatgc acagaataaa aagaattgaa      60
agtgaaaact taaggatcca aaatgaacag                                      90

<210> SEQ ID NO 27
<211> LENGTH: 160
<212> TYPE: DNA
<213> ORGANISM: Homo sapiens

<400> SEQUENCE: 27
aaaaaagctg ctaaaagaga agaagcatta gcatcatttg aggcctggaa ggctatgaaa      60
gaaaaggaag caaagaaaat agctgccaaa aagaggcttg aagaaaaaaa caagaagaaa     120
actgaagaag aaaatgctgc aagaaaagga gaagcactac                          160

<210> SEQ ID NO 28
<211> LENGTH: 146
<212> TYPE: DNA
<213> ORGANISM: Homo sapiens

<400> SEQUENCE: 28
gcttttgaaa aatggaaaga gaaaagatg gaatatctta aagagaaaaa tagaaaggag       60
agagaatatg aaagagcaaa gaaacagaaa gaggaggaaa ctgttgccga gaaaagaaa     120 gataatttaa ctgctgttga gaaatg                                         146

<210> SEQ ID NO 29
<211> LENGTH: 133
<212> TYPE: DNA
<213> ORGANISM: Homo sapiens

<400> SEQUENCE: 29
gaatgaaaaa aaggaagctt ttttcaagca aaggaaaaa gaaaaaataa atgagaaaag       60 aaggaagaa ctgaaaagag ctgagaaaaa agataaagat aaacaagcta ttaatgaata     120
tgaaaaatgg ctg                                                       133

<210> SEQ ID NO 30
```

<211> LENGTH: 485
<212> TYPE: DNA
<213> ORGANISM: Homo sapiens

<400> SEQUENCE: 30

```
gaaaataagg aaaaacaaga aagaattgaa cgaaaacaga agaaacgtca ttcctttctt      60
gaaagtgagg cacttcctcc gtggagccct ccaagcagaa ctgtgttcgc aaaagtgttt     120
tgataattct agttcttaca ttatttggtt atttatcggt ttgccaatat tagccataga    180
tttaaaacca ttcaattatt tatagttaga ggaatatatt ttaattaaat gccagacact    240
cctgctgaca atgaaagaaa tactttggaa tgtaatcagt gaaagcattt ttttgaactg    300
tagataaact gcctcaaaca aagacctaat aatcagattg ttttaccat taagatacat     360
aagattttat catgtcctga taattctat ggtggagtga ttcatgatct ttttcattaa     420
gctctgtatg ttatttaagt atatttaatt ccagtaataa aaaggaaatc atctaggtac    480
cataa                                                                485
```

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

```
atgtctgatg aagttttag cacc                                              24
```

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
aggcctcaaa tgatgctaat gc                                               22
```

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

```
atcatttgag gcctggaagg c                                                21
```

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

```
aaacactttt gcgaacacag ttc                                              23
```

<210> SEQ ID NO 35
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
acaacgaata acagagtgtc c                                            21

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
actcctgata aacagctgcc                                              20

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gccaccatgt ctgatgaagt ttttagcac                                    29

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gaaacacttt tgcgaacaca gttc                                         24

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
taatgtctga tgaagttttt agcacc                                       26

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tcaaaacact tttgcgaaca cagttc                                       26

<210> SEQ ID NO 41
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 41
aatgtctgat gaagttttta gcacc                                           25

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tcagcttgcc gtaggtggc                                                  19

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
atggtcctgc tggagttcg                                                  19

<210> SEQ ID NO 44
<211> LENGTH: 391
<212> TYPE: DNA
<213> ORGANISM: Mus musculus

<400> SEQUENCE: 44
aaagaagtga agacagaaac acgaagaata aaaagacaac gaataacaga gtgtccagtg     60
cctctggcag gctgatgacc tctgagtttt taaagagatc cggtcccaca aaaagaagtc    120
catctgcagc tacctcctca cactatttag ggagtttgaa agtcttggac cagaagcaac    180
cacggaagca gagcctagag ccagacaagg ctgatcacat aagggcagct gtttatcagg    240
agtggttaga aaagaaaaat gtgtatttac atgaaatgca cagaataaaa agaattgaaa    300
gcgaaaactt gaggatccaa aatgaacaga aaaagctgc  taagagagag gaagccctgg    360
catcatttga ggcctggaag gcaatgaaag a                                   391

<210> SEQ ID NO 45
<211> LENGTH: 2767
<212> TYPE: DNA
<213> ORGANISM: Mus musculus
<220> FEATURE:
<221> NAME/KEY: CDS
<222> LOCATION: (204)..(2147)

<400> SEQUENCE: 45
gttgggtacc caagagacca ggcggttgga agtcacttcc tcccggggac gctgttgcct     60
agcaaccgcc ttctgcctcc atcttttgcc ccgcctccag gttattccaa tacctggttt    120
cccagaccgc gaggcccggg ccggggggcga cacctgtgct agagcatagc cgctgggttc    180
tcagcagaga aaaggacac acc atg tcc gat gaa atc ttc agc aca act ttg    233
                         Met Ser Asp Glu Ile Phe Ser Thr Thr Leu
                          1               5                  10 gcg tac acc aag agt cca aag gct acc aag aga act tcc ttt cag gat    281
```

```
                                                    -continued

Ala Tyr Thr Lys Ser Pro Lys Ala Thr Lys Arg Thr Ser Phe Gln Asp
             15                  20                  25 gag ctg atc aga gcc att aca gcc cgg tca gcc agg cag aga agt tcc    329
Glu Leu Ile Arg Ala Ile Thr Ala Arg Ser Ala Arg Gln Arg Ser Ser
             30                  35                  40 gaa tac tcc gat gac ttt gac agt gac gag att gtt tct tta ggt gaa    377
Glu Tyr Ser Asp Asp Phe Asp Ser Asp Glu Ile Val Ser Leu Gly Glu
             45                  50                  55 ttt tca gat acc tcg aca gat gaa agt cta gtt aga aaa aag atg aat    425
Phe Ser Asp Thr Ser Thr Asp Glu Ser Leu Val Arg Lys Lys Met Asn
     60              65                  70 gat ttt cat ata tcc gac gat gag gaa aaa aat tct cca aga ctg tct    473
Asp Phe His Ile Ser Asp Asp Glu Glu Lys Asn Ser Pro Arg Leu Ser
 75              80                  85                  90 ttt ttg aaa acc aag aaa gta aac agg gca ata tcc aac gat gct ctg    521
Phe Leu Lys Thr Lys Lys Val Asn Arg Ala Ile Ser Asn Asp Ala Leu
             95                 100                 105 gac tcc agc act ccg ggc agc gaa ggc tcg tca ccg gat gct caa gaa    569
Asp Ser Ser Thr Pro Gly Ser Glu Gly Ser Ser Pro Asp Ala Gln Glu
            110                 115                 120 gat gtg act gga gat tcc ctc ccc aaa tct caa aat gat gat cga gaa    617
Asp Val Thr Gly Asp Ser Leu Pro Lys Ser Gln Asn Asp Asp Arg Glu
            125                 130                 135 gtc ggc aga gag atc atc aca gtg aag cct aca ccc agg atg cac ccc    665
Val Gly Arg Glu Ile Ile Thr Val Lys Pro Thr Pro Arg Met His Pro
    140                 145                 150 gtc aaa aga agc acg tcc tcg ggg gaa acc agc agc ggt ctt gat gca    713
Val Lys Arg Ser Thr Ser Ser Gly Glu Thr Ser Ser Gly Leu Asp Ala
155                 160                 165                 170 gat ggc cac ttt aag cct tca ccc cag cca agg agc atg tta aaa aag    761
Asp Gly His Phe Lys Pro Ser Pro Gln Pro Arg Ser Met Leu Lys Lys
            175                 180                 185 agc agc cac act gag gag gga gtc aga cca gga gtt gat aaa gaa cat    809
Ser Ser His Thr Glu Glu Gly Val Arg Pro Gly Val Asp Lys Glu His
            190                 195                 200 tcc ata agc gaa gcc tct gct ccc aca cct tcc ctt cca agg cag aat    857
Ser Ile Ser Glu Ala Ser Ala Pro Thr Pro Ser Leu Pro Arg Gln Asn
            205                 210                 215 ggc aca gag ttg caa act gag gaa aaa ata tac tcg gaa aac ctc gat    905
Gly Thr Glu Leu Gln Thr Glu Glu Lys Ile Tyr Ser Glu Asn Leu Asp
    220                 225                 230 ctt gag gac tca ctc tta caa agt ctg acc tca tct tcc ttc aaa gaa    953
Leu Glu Asp Ser Leu Leu Gln Ser Leu Thr Ser Ser Ser Phe Lys Glu
235                 240                 245                 250 agc ccc gga ggt tgc aca tca cca gga tct cag gaa aag gtg ccc ata   1001
Ser Pro Gly Gly Cys Thr Ser Pro Gly Ser Gln Glu Lys Val Pro Ile
            255                 260                 265 aaa gat cat gat gga gaa cct act gaa atc tgg gat tcc ttg cta tca   1049
Lys Asp His Asp Gly Glu Pro Thr Glu Ile Trp Asp Ser Leu Leu Ser
            270                 275                 280 aat gaa aat gaa gga agt tct gtt ttg gtg aac tgt gtt act cct gaa   1097
Asn Glu Asn Glu Gly Ser Ser Val Leu Val Asn Cys Val Thr Pro Glu
            285                 290                 295 ctc gag cag ccc aag gac ggt cag gtg gca gct gac gac ctt gag gaa   1145
Leu Glu Gln Pro Lys Asp Gly Gln Val Ala Ala Asp Asp Leu Glu Glu
            300                 305                 310 gaa aga gag aag ggt gga ttt aca gaa gat gac ctc acc act gac ccg   1193
Glu Arg Glu Lys Gly Gly Phe Thr Glu Asp Asp Leu Thr Thr Asp Pro
315                 320                 325                 330
```

```
ctg ctc tcc acg tcc ccg agt gtc ata aca ccc act gag cca gca gag    1241
Leu Leu Ser Thr Ser Pro Ser Val Ile Thr Pro Thr Glu Pro Ala Glu
            335                 340                 345 ccg gcc aag aaa gca aat gaa gac aga aac acg aag aat aaa aag aca    1289
Pro Ala Lys Lys Ala Asn Glu Asp Arg Asn Thr Lys Asn Lys Lys Thr
        350                 355                 360 acg aat aac aga gtg tcc agt gcc tct ggc agc agg ctg atg acc tct    1337
Thr Asn Asn Arg Val Ser Ser Ala Ser Gly Ser Arg Leu Met Thr Ser
    365                 370                 375 gag ttt tta aag aga tcc ggt ccc aca aaa aga agt cca tct gca gct    1385
Glu Phe Leu Lys Arg Ser Gly Pro Thr Lys Arg Ser Pro Ser Ala Ala
380                 385                 390 acc tcc tca cac tat tta ggg agt ttg aaa gtc ttg gac cag aag caa    1433
Thr Ser Ser His Tyr Leu Gly Ser Leu Lys Val Leu Asp Gln Lys Gln
395                 400                 405                 410 cca cgg aag cag agc cta gag cca gac aag gct gat cac ata agg gca    1481
Pro Arg Lys Gln Ser Leu Glu Pro Asp Lys Ala Asp His Ile Arg Ala
                415                 420                 425 gct gtt tat cag gag tgg tta gaa aag aaa aat gtg tat tta cat gaa    1529
Ala Val Tyr Gln Glu Trp Leu Glu Lys Lys Asn Val Tyr Leu His Glu
            430                 435                 440 atg cac aga ata aaa aga att gaa agc gaa aac ttg agg atc caa aat    1577
Met His Arg Ile Lys Arg Ile Glu Ser Glu Asn Leu Arg Ile Gln Asn
        445                 450                 455 gaa cag aaa aaa gct gct aag aga gag gaa gcc ctg gca tca ttt gag    1625
Glu Gln Lys Lys Ala Ala Lys Arg Glu Glu Ala Leu Ala Ser Phe Glu
    460                 465                 470 gcc tgg aag gca atg aaa gag aag gaa gca aag aga ata gct gca aaa    1673
Ala Trp Lys Ala Met Lys Glu Lys Glu Ala Lys Arg Ile Ala Ala Lys
475                 480                 485                 490 aag agg ctg gag gaa aag aac aag aag aaa aca gaa gaa gaa aat gcc    1721
Lys Arg Leu Glu Glu Lys Asn Lys Lys Lys Thr Glu Glu Glu Asn Ala
                495                 500                 505 atg agg aaa ggc gag gcc ctg caa gca ttt gaa aaa tgg aaa gag aaa    1769
Met Arg Lys Gly Glu Ala Leu Gln Ala Phe Glu Lys Trp Lys Glu Lys
            510                 515                 520 aag cta gaa tac ctc aaa gag aag acc agg agg gag aaa gaa tat gaa    1817
Lys Leu Glu Tyr Leu Lys Glu Lys Thr Arg Arg Glu Lys Glu Tyr Glu
        525                 530                 535 aga gca aag aaa cag aaa gaa gag gaa gcg gtt gct gag aaa aag aaa    1865
Arg Ala Lys Lys Gln Lys Glu Glu Glu Ala Val Ala Glu Lys Lys Lys
    540                 545                 550 gac agt tta act gct ttt gaa aaa tgg agt gag aga aag gaa gct ctc    1913
Asp Ser Leu Thr Ala Phe Glu Lys Trp Ser Glu Arg Lys Glu Ala Leu
555                 560                 565                 570 ctc aag caa aag gag aag gag aaa ata aat gag aga aga aag gaa gag    1961
Leu Lys Gln Lys Glu Lys Glu Lys Ile Asn Glu Arg Arg Lys Glu Glu
                575                 580                 585 ctg aag aga gcc gag aag aaa gac aaa gac aag caa gcc atc agt gaa    2009
Leu Lys Arg Ala Glu Lys Lys Asp Lys Asp Lys Gln Ala Ile Ser Glu
            590                 595                 600 tac gaa aag tgg ctg gaa aag aaa gaa agg caa gaa aga att gaa cgg    2057
Tyr Glu Lys Trp Leu Glu Lys Lys Glu Arg Gln Glu Arg Ile Glu Arg
        605                 610                 615 aaa cag aag aag cgc cac tcc ttc ctt gag agc gag aca cac cca cca    2105
Lys Gln Lys Lys Arg His Ser Phe Leu Glu Ser Glu Thr His Pro Pro
    620                 625                 630 tgg agt cct ccg agc aga act gcg ccc tca aaa gta ttt tga            2147
Trp Ser Pro Pro Ser Arg Thr Ala Pro Ser Lys Val Phe
635                 640                 645
```

-continued

```
tgtttctggt tcttgatttt ttttcagtt caccaactgt actcatggat ttaaaacgag    2207
tcatctcatt atttgtggtt agaagactct atgtcacttc cctgcaggag cttctgtgga    2267
gcatgaaaga gatactttgc agtttaatca gtggaaacat tttctgaagt gtcctcatca    2327
gtttgctggg acaatccaga cgcatgaagc tttattatga cctgaacagt ctggtgtggg    2387
gtgattcgtg gtcactgtcg ctgagttcgg agtctttta aagaatgttt gatcccacta    2447
atgaaagaat gccagctaga taccacaatc gtagagatga ctcggtctgt ggaagtctgt    2507
gcttctagag tgtagtttgg gcattgaagg tccctggaga ccatgggcat gttatctctt    2567
ctaactccag ttcttcaggt cacagaagta tctttgctgt gcaagttatc gactcagtca    2627
gttgaggcca cagaactcta gtcagtcact ttagtaaaga actttgccat agggtttaat    2687
ctcggtgtgg tttgccttct tgaggcttac ctgacaatcg tagccacctc tataatgggc    2747
tcacttctgg aatgttcttt                                                2767
```

<210> SEQ ID NO 46
<211> LENGTH: 647
<212> TYPE: PRT
<213> ORGANISM: Mus musculus

<400> SEQUENCE: 46

```
Met Ser Asp Glu Ile Phe Ser Thr Thr Leu Ala Tyr Thr Lys Ser Pro
  1               5                  10                  15

Lys Ala Thr Lys Arg Thr Ser Phe Gln Asp Glu Leu Ile Arg Ala Ile
             20                  25                  30

Thr Ala Arg Ser Ala Arg Gln Arg Ser Ser Glu Tyr Ser Asp Asp Phe
         35                  40                  45

Asp Ser Asp Glu Ile Val Ser Leu Gly Glu Phe Ser Asp Thr Ser Thr
     50                  55                  60

Asp Glu Ser Leu Val Arg Lys Lys Met Asn Asp Phe His Ile Ser Asp
 65                  70                  75                  80

Asp Glu Glu Lys Asn Ser Pro Arg Leu Ser Phe Leu Lys Thr Lys Lys
                 85                  90                  95

Val Asn Arg Ala Ile Ser Asn Asp Ala Leu Asp Ser Ser Thr Pro Gly
            100                 105                 110

Ser Glu Gly Ser Ser Pro Asp Ala Gln Glu Asp Val Thr Gly Asp Ser
        115                 120                 125

Leu Pro Lys Ser Gln Asn Asp Asp Arg Glu Val Gly Arg Glu Ile Ile
    130                 135                 140

Thr Val Lys Pro Thr Pro Arg Met His Pro Val Lys Arg Ser Thr Ser
145                 150                 155                 160

Ser Gly Glu Thr Ser Ser Gly Leu Asp Ala Asp Gly His Phe Lys Pro
                165                 170                 175

Ser Pro Gln Pro Arg Ser Met Leu Lys Lys Ser Ser His Thr Glu Glu
            180                 185                 190

Gly Val Arg Pro Gly Val Asp Lys Glu His Ser Ile Ser Glu Ala Ser
        195                 200                 205

Ala Pro Thr Pro Ser Leu Pro Arg Gln Asn Gly Thr Glu Leu Gln Thr
    210                 215                 220

Glu Glu Lys Ile Tyr Ser Glu Asn Leu Asp Leu Glu Asp Ser Leu Leu
225                 230                 235                 240

Gln Ser Leu Thr Ser Ser Ser Phe Lys Glu Ser Pro Gly Gly Cys Thr
                245                 250                 255
```

```
Ser Pro Gly Ser Gln Glu Lys Val Pro Ile Lys Asp His Asp Gly Glu
            260                 265                 270

Pro Thr Glu Ile Trp Asp Ser Leu Ser Asn Glu Asn Glu Gly Ser
        275                 280                 285

Ser Val Leu Val Asn Cys Val Thr Pro Glu Leu Glu Gln Pro Lys Asp
    290                 295                 300

Gly Gln Val Ala Ala Asp Asp Leu Glu Glu Arg Glu Lys Gly Gly
305                 310                 315                 320

Phe Thr Glu Asp Asp Leu Thr Thr Asp Pro Leu Leu Ser Thr Ser Pro
                325                 330                 335

Ser Val Ile Thr Pro Thr Glu Pro Ala Glu Pro Ala Lys Lys Ala Asn
            340                 345                 350

Glu Asp Arg Asn Thr Lys Asn Lys Thr Thr Asn Asn Arg Val Ser
        355                 360                 365

Ser Ala Ser Gly Ser Arg Leu Met Thr Ser Glu Phe Leu Lys Arg Ser
    370                 375                 380

Gly Pro Thr Lys Arg Ser Pro Ser Ala Ala Thr Ser Ser His Tyr Leu
385                 390                 395                 400

Gly Ser Leu Lys Val Leu Asp Gln Lys Gln Pro Arg Lys Gln Ser Leu
                405                 410                 415

Glu Pro Asp Lys Ala Asp His Ile Arg Ala Ala Val Tyr Gln Glu Trp
            420                 425                 430

Leu Glu Lys Lys Asn Val Tyr Leu His Glu Met His Arg Ile Lys Arg
        435                 440                 445

Ile Glu Ser Glu Asn Leu Arg Ile Gln Asn Glu Gln Lys Lys Ala Ala
    450                 455                 460

Lys Arg Glu Glu Ala Leu Ala Ser Phe Glu Ala Trp Lys Ala Met Lys
465                 470                 475                 480

Glu Lys Glu Ala Lys Arg Ile Ala Ala Lys Arg Leu Glu Glu Lys
                485                 490                 495

Asn Lys Lys Lys Thr Glu Glu Asn Ala Met Arg Lys Gly Glu Ala
            500                 505                 510

Leu Gln Ala Phe Glu Lys Trp Lys Glu Lys Leu Glu Tyr Leu Lys
        515                 520                 525

Glu Lys Thr Arg Arg Glu Lys Glu Tyr Glu Arg Ala Lys Lys Gln Lys
        530                 535                 540

Glu Glu Glu Ala Val Ala Glu Lys Lys Asp Ser Leu Thr Ala Phe
545                 550                 555                 560

Glu Lys Trp Ser Glu Arg Lys Glu Ala Leu Leu Lys Gln Lys Glu Lys
                565                 570                 575

Glu Lys Ile Asn Glu Arg Arg Lys Glu Glu Leu Lys Arg Ala Glu Lys
            580                 585                 590

Lys Asp Lys Asp Lys Gln Ala Ile Ser Glu Tyr Glu Lys Trp Leu Glu
        595                 600                 605

Lys Lys Glu Arg Gln Glu Arg Ile Glu Arg Lys Gln Lys Arg His
        610                 615                 620

Ser Phe Leu Glu Ser Glu Thr His Pro Pro Trp Ser Pro Pro Ser Arg
625                 630                 635                 640

Thr Ala Pro Ser Lys Val Phe
                645
```

<210> SEQ ID NO 47
<211> LENGTH: 647
<212> TYPE: PRT

<213> ORGANISM: Mus musculus

<400> SEQUENCE: 47

```
Met Ser Asp Glu Ile Phe Ser Thr Thr Leu Ala Tyr Thr Lys Ser Pro
  1               5                  10                  15
Lys Ala Thr Lys Arg Thr Ser Phe Gln Asp Glu Leu Ile Arg Ala Ile
                 20                  25                  30
Thr Ala Arg Ser Ala Arg Gln Arg Ser Glu Tyr Ser Asp Asp Phe
             35                  40                  45
Asp Ser Asp Glu Ile Val Ser Leu Gly Glu Phe Ser Asp Thr Ser Thr
 50                  55                  60
Asp Glu Ser Leu Val Arg Lys Lys Met Asn Asp Phe His Ile Ser Asp
 65                  70                  75                  80
Asp Glu Glu Lys Asn Ser Pro Arg Leu Ser Phe Leu Lys Thr Lys Lys
                 85                  90                  95
Val Asn Arg Ala Ile Ser Asn Asp Ala Leu Asp Ser Ser Thr Pro Gly
                100                 105                 110
Ser Glu Gly Ser Ser Pro Asp Ala Gln Glu Asp Val Thr Gly Asp Ser
            115                 120                 125
Leu Pro Lys Ser Gln Asn Asp Asp Arg Glu Val Gly Arg Glu Ile Ile
130                 135                 140
Thr Val Lys Pro Thr Pro Arg Met His Pro Val Lys Arg Ser Thr Ser
145                 150                 155                 160
Ser Gly Glu Thr Ser Ser Gly Leu Asp Ala Asp Gly His Phe Lys Pro
                165                 170                 175
Ser Pro Gln Pro Arg Ser Met Leu Lys Lys Ser Ser His Thr Glu Glu
            180                 185                 190
Gly Val Arg Pro Gly Val Asp Lys Glu His Ser Ile Ser Glu Ala Ser
            195                 200                 205
Ala Pro Thr Pro Ser Leu Pro Arg Gln Asn Gly Thr Glu Leu Gln Thr
210                 215                 220
Glu Glu Lys Ile Tyr Ser Glu Asn Leu Asp Leu Glu Asp Ser Leu Leu
225                 230                 235                 240
Gln Ser Leu Thr Ser Ser Ser Phe Lys Glu Ser Pro Gly Gly Cys Thr
                245                 250                 255
Ser Pro Gly Ser Gln Glu Lys Val Pro Ile Lys Asp His Asp Gly Glu
            260                 265                 270
Pro Thr Glu Ile Trp Asp Ser Leu Leu Ser Asn Glu Asn Glu Gly Ser
            275                 280                 285
Ser Val Leu Val Asn Cys Val Thr Pro Glu Leu Glu Gln Pro Lys Asp
290                 295                 300
Gly Gln Val Ala Ala Asp Asp Leu Glu Glu Glu Arg Glu Lys Gly Gly
305                 310                 315                 320
Phe Thr Glu Asp Asp Leu Thr Thr Asp Pro Leu Leu Ser Thr Ser Pro
                325                 330                 335
Ser Val Ile Thr Pro Thr Glu Pro Ala Glu Pro Ala Lys Lys Ala Asn
            340                 345                 350
Glu Asp Arg Asn Thr Lys Asn Lys Lys Thr Thr Asn Asn Arg Val Ser
            355                 360                 365
Ser Ala Ser Gly Ser Arg Leu Met Thr Ser Glu Phe Leu Lys Arg Ser
370                 375                 380
Gly Pro Thr Lys Arg Ser Pro Ser Ala Ala Thr Ser Ser His Tyr Leu
385                 390                 395                 400
```

```
Gly Ser Leu Lys Val Leu Asp Gln Lys Gln Pro Arg Lys Gln Ser Leu
                405                 410                 415

Glu Pro Asp Lys Ala Asp His Ile Arg Ala Ala Val Tyr Gln Glu Trp
            420                 425                 430

Leu Glu Lys Lys Asn Val Tyr Leu His Glu Met His Arg Ile Lys Arg
        435                 440                 445

Ile Glu Ser Glu Asn Leu Arg Ile Gln Asn Glu Gln Lys Lys Ala Ala
    450                 455                 460

Lys Arg Glu Glu Ala Leu Ala Ser Phe Glu Ala Trp Lys Ala Met Lys
465                 470                 475                 480

Glu Lys Glu Ala Lys Arg Ile Ala Ala Lys Arg Leu Glu Glu Lys
                485                 490                 495

Asn Lys Lys Lys Thr Glu Glu Asn Ala Met Arg Lys Gly Glu Ala
                500                 505                 510

Leu Gln Ala Phe Glu Lys Trp Lys Glu Lys Leu Glu Tyr Leu Lys
    515                 520                 525

Glu Lys Thr Arg Arg Glu Lys Glu Tyr Glu Arg Ala Lys Lys Gln Lys
    530                 535                 540

Glu Glu Glu Ala Val Ala Glu Lys Lys Lys Asp Ser Leu Thr Ala Phe
545                 550                 555                 560

Glu Lys Trp Ser Glu Arg Lys Glu Ala Leu Leu Lys Gln Lys Glu Lys
                565                 570                 575

Glu Lys Ile Asn Glu Arg Arg Lys Glu Glu Leu Lys Arg Ala Glu Lys
                580                 585                 590

Lys Asp Lys Asp Lys Gln Ala Ile Ser Glu Tyr Glu Lys Trp Leu Glu
                595                 600                 605

Lys Lys Glu Arg Gln Glu Arg Ile Glu Arg Lys Gln Lys Lys Arg His
                610                 615                 620

Ser Phe Leu Glu Ser Glu Thr His Pro Pro Trp Ser Pro Pro Ser Arg
625                 630                 635                 640

Thr Ala Pro Ser Lys Val Phe
                645

<210> SEQ ID NO 48
<211> LENGTH: 344
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 48

Glu Ser Gln Val Thr Ala Asp Asp Leu Glu Glu Glu Lys Ala Lys Ala
1               5                   10                  15

Glu Leu Ile Met Asp Asp Arg Thr Val Asp Pro Leu Leu Ser Lys
            20                  25                  30

Ser Gln Ser Ile Leu Ile Ser Thr Ser Ala Thr Ala Ser Ser Lys Lys
        35                  40                  45

Thr Ile Glu Asp Arg Asn Ile Lys Asn Lys Lys Ser Thr Asn Asn Arg
    50                  55                  60

Ala Ser Ser Ala Ser Ala Arg Leu Met Thr Ser Glu Phe Leu Lys Lys
65                  70                  75                  80

Ser Ser Ser Lys Arg Arg Thr Pro Ser Thr Thr Ser Ser His Tyr
                85                  90                  95

Leu Gly Thr Leu Lys Val Leu Asp Gln Lys Pro Ser Gln Lys Gln Ser
            100                 105                 110
```

Ile Glu Pro Asp Arg Ala Asp Asn Ile Arg Ala Ala Val Tyr Gln Glu
            115                 120                 125

Trp Leu Glu Lys Lys Asn Val Tyr Leu His Glu Met His Arg Ile Lys
        130                 135                 140

Arg Ile Glu Ser Glu Asn Leu Arg Ile Gln Asn Glu Gln Lys Lys Ala
145                 150                 155                 160

Ala Lys Arg Glu Glu Ala Leu Ala Ser Phe Glu Ala Trp Lys Ala Met
                165                 170                 175

Lys Glu Lys Glu Ala Lys Lys Ile Ala Ala Lys Lys Arg Leu Glu Glu
            180                 185                 190

Lys Asn Lys Lys Thr Glu Glu Asn Ala Ala Arg Lys Gly Glu
        195                 200                 205

Ala Leu Gln Ala Phe Glu Lys Trp Lys Glu Lys Lys Met Glu Tyr Leu
    210                 215                 220

Lys Glu Lys Asn Arg Lys Glu Arg Glu Tyr Glu Arg Ala Lys Lys Gln
225                 230                 235                 240

Lys Glu Glu Glu Thr Val Ala Glu Lys Lys Asp Asn Leu Thr Ala
                245                 250                 255

Val Glu Lys Trp Asn Glu Lys Lys Glu Ala Phe Phe Lys Gln Lys Lys
            260                 265                 270

Lys Glu Lys Ile Asn Glu Lys Arg Lys Glu Glu Leu Lys Arg Ala Glu
        275                 280                 285

Lys Lys Asp Lys Asp Lys Gln Ala Ile Asn Glu Tyr Glu Lys Trp Leu
    290                 295                 300

Glu Asn Lys Glu Lys Gln Glu Arg Ile Glu Arg Lys Gln Lys Arg
305                 310                 315                 320

His Ser Phe Leu Glu Ser Glu Ala Leu Pro Pro Trp Ser Pro Pro Ser
                325                 330                 335

Arg Thr Val Phe Ala Lys Val Phe
            340

<210> SEQ ID NO 49
<211> LENGTH: 237
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 49

Ser Gln Lys Gln Ser Ile Glu Pro Asp Arg Ala Asp Asn Ile Arg Ala
  1               5                  10                  15

Ala Val Tyr Gln Glu Trp Leu Glu Lys Lys Asn Val Tyr Leu His Glu
            20                  25                  30

Met His Arg Ile Lys Arg Ile Glu Ser Glu Asn Leu Arg Ile Gln Asn
        35                  40                  45

Glu Gln Lys Lys Ala Ala Lys Arg Glu Glu Ala Leu Ala Ser Phe Glu
    50                  55                  60

Ala Trp Lys Ala Met Lys Glu Lys Glu Ala Lys Lys Ile Ala Ala Lys
65                  70                  75                  80

Lys Arg Leu Glu Glu Lys Asn Lys Lys Thr Glu Glu Asn Ala
                85                  90                  95

Ala Arg Lys Gly Glu Ala Leu Gln Ala Phe Glu Lys Trp Lys Glu Lys
            100                 105                 110

Lys Met Glu Tyr Leu Lys Glu Lys Asn Arg Lys Glu Arg Glu Tyr Glu

-continued

```
                115                 120                 125
Arg Ala Lys Lys Gln Lys Glu Glu Thr Val Ala Glu Lys Lys Lys
    130                 135                 140

Asp Asn Leu Thr Ala Val Glu Lys Trp Asn Glu Lys Lys Glu Ala Phe
145                 150                 155                 160

Phe Lys Gln Lys Lys Glu Lys Ile Asn Glu Lys Arg Lys Glu Glu
                165                 170                 175

Leu Lys Arg Ala Glu Lys Lys Asp Lys Asp Lys Gln Ala Ile Asn Glu
                180                 185                 190

Tyr Glu Lys Trp Leu Glu Asn Lys Glu Lys Gln Glu Arg Ile Glu Arg
                195                 200                 205

Lys Gln Lys Lys Arg His Ser Phe Leu Glu Ser Glu Ala Leu Pro Pro
    210                 215                 220

Trp Ser Pro Pro Ser Arg Thr Val Phe Ala Lys Val Phe
225                 230                 235

<210> SEQ ID NO 50
<211> LENGTH: 170
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 50

Ala Met Lys Glu Lys Glu Ala Lys Lys Ile Ala Ala Lys Lys Arg Leu
1               5                   10                  15

Glu Glu Lys Asn Lys Lys Lys Thr Glu Glu Glu Asn Ala Ala Arg Lys
                20                  25                  30

Gly Glu Ala Leu Gln Ala Phe Glu Lys Trp Lys Glu Lys Lys Met Glu
            35                  40                  45

Tyr Leu Lys Glu Lys Asn Arg Lys Glu Arg Glu Tyr Glu Arg Ala Lys
        50                  55                  60

Lys Gln Lys Glu Glu Glu Thr Val Ala Glu Lys Lys Lys Asp Asn Leu
65                  70                  75                  80

Thr Ala Val Glu Lys Trp Asn Glu Lys Lys Glu Ala Phe Phe Lys Gln
                85                  90                  95

Lys Lys Lys Glu Lys Ile Asn Glu Lys Arg Lys Glu Glu Leu Lys Arg
                100                 105                 110

Ala Glu Lys Lys Asp Lys Asp Lys Gln Ala Ile Asn Glu Tyr Glu Lys
            115                 120                 125

Trp Leu Glu Asn Lys Glu Lys Gln Glu Arg Ile Glu Arg Lys Gln Lys
    130                 135                 140

Lys Arg His Ser Phe Leu Glu Ser Glu Ala Leu Pro Pro Trp Ser Pro
145                 150                 155                 160

Pro Ser Arg Thr Val Phe Ala Lys Val Phe
                165                 170

<210> SEQ ID NO 51
<211> LENGTH: 477
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 51

Met Ser Asp Glu Val Phe Ser Thr Thr Leu Ala Tyr Thr Lys Ser Pro
```

-continued

```
  1               5              10              15
Lys Val Thr Lys Arg Thr Thr Phe Gln Asp Glu Leu Ile Arg Ala Ile
             20                  25                  30

Thr Ala Arg Ser Ala Arg Gln Arg Ser Ser Glu Tyr Ser Asp Asp Phe
             35                  40                  45

Asp Ser Asp Glu Ile Val Ser Leu Gly Asp Phe Ser Asp Thr Ser Ala
             50                  55                  60

Asp Glu Asn Ser Val Asn Lys Lys Met Asn Asp Phe His Ile Ser Asp
 65                  70                  75                  80

Asp Glu Glu Lys Asn Pro Ser Lys Leu Leu Phe Leu Lys Thr Asn Lys
                 85                  90                  95

Ser Asn Gly Asn Ile Thr Lys Asp Glu Pro Val Cys Ala Ile Lys Asn
                100                 105                 110

Glu Glu Glu Met Ala Pro Asp Gly Cys Glu Asp Ile Val Val Lys Ser
                115                 120                 125

Phe Ser Glu Ser Gln Asn Lys Asp Glu Glu Phe Glu Lys Asp Lys Ile
                130                 135                 140

Lys Met Lys Pro Lys Pro Arg Ile Leu Ser Ile Lys Ser Thr Ser Ser
145                 150                 155                 160

Ala Glu Asn Asn Ser Leu Asp Thr Asp Asp His Phe Lys Pro Ser Pro
                165                 170                 175

Trp Pro Arg Ser Met Leu Lys Lys Lys Ser His Met Glu Glu Lys Asp
                180                 185                 190

Gly Leu Glu Asp Lys Glu Thr Ala Leu Ser Glu Glu Leu Glu Leu His
                195                 200                 205

Ser Ala Pro Ser Ser Leu Pro Thr Pro Asn Gly Ile Gln Leu Glu Ala
                210                 215                 220

Glu Lys Lys Ala Phe Ser Glu Asn Leu Asp Pro Glu Asp Ser Cys Leu
225                 230                 235                 240

Thr Ser Leu Ala Ser Ser Leu Lys Gln Ile Leu Gly Asp Ser Phe
                245                 250                 255

Ser Pro Gly Ser Glu Gly Asn Ala Ser Gly Lys Asp Pro Asn Glu Glu
                260                 265                 270

Ile Thr Glu Asn His Asn Ser Leu Lys Ser Asp Glu Asn Lys Glu Asn
                275                 280                 285

Ser Phe Ser Ala Asp His Val Thr Ala Val Glu Lys Ser Lys Glu
                290                 295                 300

Ser Gln Val Thr Ala Asp Asp Leu Glu Glu Glu Lys Ala Lys Ala Glu
305                 310                 315                 320

Leu Ile Met Asp Asp Asp Arg Thr Val Asp Pro Leu Leu Ser Lys Ser
                325                 330                 335

Gln Ser Ile Leu Ile Ser Thr Ser Ala Thr Ala Ser Ser Lys Lys Thr
                340                 345                 350

Ile Glu Asp Arg Asn Ile Lys Asn Lys Ser Thr Asn Asn Arg Ala
                355                 360                 365

Ser Ser Ala Ser Ala Arg Leu Met Thr Ser Glu Phe Leu Lys Lys Ser
    370                 375                 380

Ser Ser Lys Arg Arg Thr Pro Ser Thr Thr Ser Ser His Tyr Leu
385                 390                 395                 400

Gly Thr Leu Lys Val Leu Asp Gln Lys Pro Ser Gln Lys Gln Ser Ile
                405                 410                 415

Glu Pro Asp Arg Ala Asp Asn Ile Arg Ala Ala Val Tyr Gln Glu Trp
                420                 425                 430
```

```
Leu Glu Lys Lys Asn Val Tyr Leu His Glu Met His Arg Ile Lys Arg
            435                 440                 445

Ile Glu Ser Glu Asn Leu Arg Ile Gln Asn Glu Gln Lys Lys Ala Ala
            450                 455                 460

Lys Arg Glu Glu Ala Leu Ala Ser Phe Glu Ala Trp Lys
465                 470                 475

<210> SEQ ID NO 52
<211> LENGTH: 418
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 52

Met Ser Asp Glu Val Phe Ser Thr Thr Leu Ala Tyr Thr Lys Ser Pro
  1               5                  10                  15

Lys Val Thr Lys Arg Thr Thr Phe Gln Asp Glu Leu Ile Arg Ala Ile
             20                  25                  30

Thr Ala Arg Ser Ala Arg Gln Arg Ser Ser Glu Tyr Ser Asp Asp Phe
         35                  40                  45

Asp Ser Asp Glu Ile Val Ser Leu Gly Asp Phe Ser Asp Thr Ser Ala
     50                  55                  60

Asp Glu Asn Ser Val Asn Lys Lys Met Asn Asp Phe His Ile Ser Asp
 65                  70                  75                  80

Asp Glu Glu Lys Asn Pro Ser Lys Leu Leu Phe Leu Lys Thr Asn Lys
                 85                  90                  95

Ser Asn Gly Asn Ile Thr Lys Asp Glu Pro Val Cys Ala Ile Lys Asn
            100                 105                 110

Glu Glu Glu Met Ala Pro Asp Gly Cys Glu Asp Ile Val Val Lys Ser
        115                 120                 125

Phe Ser Glu Ser Gln Asn Lys Asp Glu Glu Phe Glu Lys Asp Lys Ile
    130                 135                 140

Lys Met Lys Pro Lys Pro Arg Ile Leu Ser Ile Lys Ser Thr Ser Ser
145                 150                 155                 160

Ala Glu Asn Asn Ser Leu Asp Thr Asp Asp His Phe Lys Pro Ser Pro
                165                 170                 175

Trp Pro Arg Ser Met Leu Lys Lys Lys Ser His Met Glu Glu Lys Asp
            180                 185                 190

Gly Leu Glu Asp Lys Glu Thr Ala Leu Ser Glu Glu Leu Glu Leu His
        195                 200                 205

Ser Ala Pro Ser Ser Leu Pro Thr Pro Asn Gly Ile Gln Leu Glu Ala
    210                 215                 220

Glu Lys Lys Ala Phe Ser Glu Asn Leu Asp Pro Glu Asp Ser Cys Leu
225                 230                 235                 240

Thr Ser Leu Ala Ser Ser Leu Lys Gln Ile Leu Gly Asp Ser Phe
                245                 250                 255

Ser Pro Gly Ser Glu Gly Asn Ala Ser Gly Lys Asp Pro Asn Glu Glu
            260                 265                 270

Ile Thr Glu Asn His Asn Ser Leu Lys Ser Asp Glu Asn Lys Glu Asn
        275                 280                 285

Ser Phe Ser Ala Asp His Val Thr Thr Ala Val Glu Lys Ser Lys Glu
    290                 295                 300

Ser Gln Val Thr Ala Asp Asp Leu Glu Glu Glu Lys Ala Lys Ala Glu
```

```
                305                 310                 315                 320
Leu Ile Met Asp Asp Asp Arg Thr Val Asp Pro Leu Leu Ser Lys Ser
                325                 330                 335

Gln Ser Ile Leu Ile Ser Thr Ser Ala Thr Ala Ser Ser Lys Lys Thr
                340                 345                 350

Ile Glu Asp Arg Asn Ile Lys Asn Lys Lys Ser Thr Asn Asn Arg Ala
                355                 360                 365

Ser Ser Ala Ser Ala Arg Leu Met Thr Ser Glu Phe Leu Lys Lys Ser
                370                 375                 380

Ser Ser Lys Arg Arg Thr Pro Ser Thr Thr Ser Ser His Tyr Leu
385                 390                 395                 400

Gly Thr Leu Lys Val Leu Asp Gln Lys Pro Ser Gln Lys Gln Ser Ile
                405                 410                 415

Glu Pro

<210> SEQ ID NO 53
<211> LENGTH: 303
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 53

Met Ser Asp Glu Val Phe Ser Thr Thr Leu Ala Tyr Thr Lys Ser Pro
1               5                   10                  15

Lys Val Thr Lys Arg Thr Thr Phe Gln Asp Glu Leu Ile Arg Ala Ile
                20                  25                  30

Thr Ala Arg Ser Ala Arg Gln Arg Ser Ser Glu Tyr Ser Asp Asp Phe
            35                  40                  45

Asp Ser Asp Glu Ile Val Ser Leu Gly Asp Phe Ser Asp Thr Ser Ala
        50                  55                  60

Asp Glu Asn Ser Val Asn Lys Lys Met Asn Asp Phe His Ile Ser Asp
65                  70                  75                  80

Asp Glu Glu Lys Asn Pro Ser Lys Leu Leu Phe Leu Lys Thr Asn Lys
                85                  90                  95

Ser Asn Gly Asn Ile Thr Lys Asp Glu Pro Val Cys Ala Ile Lys Asn
                100                 105                 110

Glu Glu Glu Met Ala Pro Asp Gly Cys Glu Asp Ile Val Val Lys Ser
            115                 120                 125

Phe Ser Glu Ser Gln Asn Lys Asp Glu Glu Phe Glu Lys Asp Lys Ile
        130                 135                 140

Lys Met Lys Pro Lys Pro Arg Ile Leu Ser Ile Lys Ser Thr Ser Ser
145                 150                 155                 160

Ala Glu Asn Asn Ser Leu Asp Thr Asp Asp His Phe Lys Pro Ser Pro
                165                 170                 175

Trp Pro Arg Ser Met Leu Lys Lys Ser His Met Glu Glu Lys Asp
                180                 185                 190

Gly Leu Glu Asp Lys Glu Thr Ala Leu Ser Glu Glu Leu His
            195                 200                 205

Ser Ala Pro Ser Ser Leu Pro Thr Pro Asn Gly Ile Gln Leu Glu Ala
        210                 215                 220

Glu Lys Lys Ala Phe Ser Glu Asn Leu Asp Pro Glu Asp Ser Cys Leu
225                 230                 235                 240

Thr Ser Leu Ala Ser Ser Ser Leu Lys Gln Ile Leu Gly Asp Ser Phe
```

```
                       245                 250                 255

Ser Pro Gly Ser Glu Gly Asn Ala Ser Gly Lys Asp Pro Asn Glu Glu
                260                 265                 270

Ile Thr Glu Asn His Asn Ser Leu Lys Ser Asp Glu Asn Lys Glu Asn
            275                 280                 285

Ser Phe Ser Ala Asp His Val Thr Thr Ala Val Glu Lys Ser Lys
        290                 295                 300
```

CENTROSOME-ASSOCIATED PROTEIN AND APPLICATIONS THEREOF

The present invention relates to a novel centrosome-associated protein, to the polynucleotide encoding said protein and also to the applications of said protein and of said polynucleotide.

The cell division process consists of a nuclear division (mitosis) followed by a cytoplasmic division (cytokinesis). The mitosis is dominated by the formation of a very organized polar spindle (the mitotic spindle) consisting of two families of microtubules: polar microtubules and kinetochore microtubules. Microtubules are polymers made up of α- and β-tubulin subunits. Their growth is initiated in the peripheral region of the centrosome by a complex containing mainly a related protein, γ-tubulin. Polar microtubules are made up of rows of microtubules and of associated-proteins which are put in place by the two mitotic centers, associated with centrioles, located at opposite poles of the spindle (asters). Each replicated chromosome consists of two sister chromatids connected to one another via the centromere. Kinetochore microtubules are attached to the replicated chromosomes by means of specialized structures called kinetochores, which form during prophase on each of the two faces of the centromere. The chromosomes condense during prophase and form the kinetochore microtubules, which begin to interact with the polar microtubules of the spindle after rupture of the nuclear envelope during prometaphase. Under the effect of the tension due to the opposite forces, directed toward the poles, which pull the kinetochore microtubules, the chromosomes align in the equatorial zone of the spindle during metaphase. In anaphase, under the effect of forces that are continually developed within the mitotic spindle, the sister chromatids detach and are drawn toward the opposite poles. At the same time, the two cellular poles move apart. During telophase, the nuclear envelope re-forms at the surface of each group of chromosomes.

Cell division comes to an end when the cytoplasmic content is divided according to the process of cytokinesis. The mitotic spindle plays an important role in the process of cytokinesis, by fixing the setting up of cell segmentation. The cleavage furrow invariably appears in the plane of the equatorial plate, perpendicular to the axis of the mitotic spindle.

The processes described above are finely regulated by an equilibrium between phosphorylation reactions and dephosphorylation reactions. When the cell enters into mitosis, important changes in the phosphorylation of the proteins occur. The centrosome and the mitotic spindle are particularly enriched in phosphorylated sites. Many protein kinases, particularly serine-threonine kinases, have been described as being involved in these phosphorylation processes (in this respect, see R. Giet and C. Prigent, J. Cell Science, 112, 3591-3601, 1999). Among these, mention will be made of those located at the level of the centrosomes, among which, aurora-type kinases, that are required for centrosome separation and mitotic spindle assembly, polo-type kinases, that are involved in the maturation and formation of the bipolar spindle, and NIMA-type kinases, that regulate centrosome separation.

Mammals have at least three aurora-type protein kinases. In humans, these three protein kinases are overexpressed in cancer-related pathologies due to chromosomal anomalies. Thus, these proteins appear to play an important role in the control of ploidy. For example, inactivation or overexpression of two of these kinases results in polyploidy. Inhibition of the activity of the aurora A kinase results in the formation of monopolar spindles. Inhibition of the activity of the aurora B kinase results in the formation of multinuclear cells through lack of cytokinesis. These chromosomal anomalies appear to be associated with disturbances in mitotic spindle formation.

The partners and the substrates of these protein kinases are still relatively unknown. For example, in xenopus, aurora A interacts with a kinesin involved in microtubule dynamics. In humans, it phosphorylates the HsTACC-3 protein, also overexpressed in many cancer cell lines. In *drosophila*, aurora A phosphorylates the D-TACC protein and is necessary for the localization thereof at the centrosomes in order to regulate astral microtubules. D-TACC interacts with the microtubule-associated protein (MAP) Msp, which is part of the family of XMA0215/ch-TOC/Msps proteins, which stimulate microtubule growth in vitro and are concentrated in the centromeres in vivo. D-TACC and Msp cooperate in order to stabilize centrosomes. The term "MAP" includes a collection of varied proteins defined on the basis of their ability to interact with microtubules. MAPs appear to be partners/substrates of the kinases of the centrosome, such as aurora or polo.

Correct cell division requires coordination between chromosomal segregation by the mitotic spindle and cell cleavage by the cytokinetic apparatus. The microtubules of the mitotic spindle play an essential role in both processes.

However, despite all the studies carried out on cell division, the factors that are involved in correctly setting up the mitotic spindle and/or, on the contrary, that disturb the setting up and/or the structure thereof, thus leading to the consequences described above, are still not known.

Such knowledge would make it possible, firstly, to understand more thoroughly the mechanisms of mitosis and, secondly, to be able to develop means for combating cell division anomalies and their resulting consequences.

The present invention lies within this field.

SUMMARY OF THE INVENTION

Specifically, surprisingly and unexpectedly, the inventors have demonstrated a novel centrosome-associated human protein. By immunofluorescence, it is detected as a colocalization with the α-tubulin of the microtubules of the mitotic spindle, in particular with the aster. This protein was named ASAP, for Aster Associated Protein, by the inventors.

Overexpression of the protein according to the invention disturbs the organization of the mitotic spindle and induces aberrant and abortive mitoses (plurinuclear cells, monopolar or multipolar spindles). Its overexpression blocks cell division and, consequently, cell proliferation.

A subject of the invention is thus an isolated protein, called ASAP, characterized in that it is selected from the group consisting of:

a) a protein corresponding to the sequence represented in the attached sequence listing under the number SEQ ID NO: 1;

b) a protein exhibiting, over its entire sequence, at least 80% identity or at least 90% similarity, preferably at least 90% identity or at least 95% similarity, with the protein of SEQ ID NO: 1.

A protein in accordance with the invention is characterized by the following properties:
- it has a molecular weight of between 60 and 100 kDa, preferably of between 65 and 80 kDa;
- it is associated with the centrosomes;
- it is colocalized, by immunofluorescence, with the α-tubulin of the microtubules of the mitotic spindle;
- it exhibits weak identity (23%) with the MAP1A protein (Microtubule Associated Protein 1A);
- it has coiled-coil domains essentially included in its C-terminal portion between, firstly, amino acids 297 and 327 and, secondly, amino acids 477 and 628, indicating either that the protein oligomerizes, or that it interacts with other proteins;

it exhibits weak identity (20%), between amino acids 300 and 600, with a caldesmon-type domain (N. B. Gusev, Biochemistry, 10: 1112-1121, 2000), referenced pfam00769 (NCBI, domains, www.ncbi.nlm.nih.gov/Structure/cdd/cddsrv.cgi?uid-=pfam00769), and, between amino acids 480 and 630, with a domain of ERM type (ezrin/radixin/moesin; S. Louvet-Vallet, Biol. Cell, 274: 305-316, 2000), referenced pfam02029 (NCBI, domains, www.ncbi.nlm.nih.gov/Structure/cdd/cddsrv.cgi?uid-=pfam02029). The caldesmon and ERM proteins are also considered to be MAPs;

it also has, between positions 65 and 303, a BRCT domain (Breast Cancer Carboxy-Terminal domain; P. Bork et al., FASEB J., 11, 68-76 (1997)), indicating that the protein is involved in cell cycle control;

it is very rich in α-helices in its C-terminal portion, in particular in the region between amino acids 420-620, which is almost exclusively made up of α-helices.

These elements make it possible to consider that the ASAP protein is a novel MAP.

The proteins according to the invention include any protein (natural, synthetic, semi-synthetic or recombinant) of any prokaryotic or eukaryotic organism, in particular of a mammal, comprising or consisting of an ASAP protein. Preferably, said protein is a functional ASAP protein.

The term "functional" is intended to mean a protein that has normal biological activity, i.e. that is capable of being involved in mitotic spindle organization and in cell division. This protein can comprise silent mutations that do not induce any substantial change in its activity and do not produce any phenotypic modification.

Proteins in accordance with the invention are in particular represented by the human ASAP (SEQ ID NO: 1) and murine ASAP (SEQ ID NO: 46) proteins.

Included in the proteins according to the invention defined in b) are the proteins that are variants of the sequences SEQ ID NOS: 1 and 46, in particular the proteins for which the amino acid sequence has at least one mutation corresponding in particular to a truncation, a deletion, a substitution and/or an addition of at least one amino acid residue compared with the sequences SEQ ID NOS: 1 and 46.

Preferably, the variant proteins have a mutation that results in a dysfunction (activation or inhibition) of the protein, of other genes or proteins, or else of the cell in general.

According to another advantageous embodiment of the invention, said protein is a mammalian protein, preferably a protein of human origin.

For the purpose of the present invention, the following definitions apply.

The identity of a sequence relative to the sequence of SEQ ID NO: 1 as reference sequence is assessed according to the percentage of amino acid residues that are identical, when the two sequences are aligned, so as to obtain the maximum correspondence between them.

The percentage identity can be calculated by those skilled in the art using a computer program for sequence comparison such as, for example, that of the BLAST series (Altschul et al., NAR, 1997, 25, 3389-3402).

The BLAST programs are implemented over the window of comparison consisting of the entire SEQ ID NO: 1, indicated as reference sequence.

A protein having an amino acid sequence that has at least X % identity with a reference sequence is defined, in the present invention, as a protein whose sequence can include up to 100-X alterations per 100 amino acids of the reference sequence, while at the same time conserving the functional properties of said reference protein. For the purpose of the present invention, the term "alteration" includes consecutive or dispersed deletions, substitutions or insertions of amino acids in the reference sequence.

The similarity of a sequence relative to a reference sequence is assessed according to the percentage of amino acid residues that are identical or that differ by means of conservative substitutions, when the two sequences are aligned so as to obtain the maximum correspondence between them. For the purpose of the present invention, the term "conservative substitution" is intended to mean the substitution of an amino acid with another that has similar chemical or physical properties (size, charge or polarity), which generally does not modify the functional properties of the protein.

A protein having an amino acid sequence that has at least X % similarity with a reference sequence is defined, in the present invention, as a protein whose sequence can include up to 100-X non-conservative alterations per 100 amino acids of the reference sequence. For the purpose of the present invention, the term "non-conservative alterations" includes consecutive or dispersed non-conservative substitutions or insertions of amino acids in the reference sequence.

The expression "techniques or methods well known to those skilled in the art" is here intended to refer to the techniques or methods conventionally used by those skilled in the art and disclosed in many works, such as in particular that entitled Molecular Cloning. A Laboratory Manual (J. Sambrook, D. W. Russell (2000) Cold Spring Harbor Laboratory Press).

The protein according to the invention is obtained either from a cell, or by chemical synthesis, or by genetic recombination.

By chemical synthesis, the protein can be obtained using one of the many known peptide synthesis pathways, for example techniques using solid phases or techniques using partial solid phases, by fragment condensation or by conventional synthesis in solution. In this case, the sequence of the protein can be modified in order to improve its solubility, in particular in aqueous solvents. Such modifications are known to those skilled in the art, for instance the deletion of hydrophobic domains or the substitution of hydrophobic amino acids with hydrophilic amino acids.

The protein according to the invention consists of the series of 13 peptides corresponding to the products of translation of 13 of the 14 exons that the corresponding gene contains, the first exon not being translated (see hereinafter).

More precisely, said peptides correspond to the following sequences (positions given relative to the numbering of the sequence SEQ ID NO: 1):

peptide 1: it comprises 25 amino acids corresponding to positions 1 to 25 (SEQ ID NO: 2);

peptide 2: it comprises 28 amino acids corresponding to positions 26 to 53 (SEQ ID NO: 3);

peptide 3: it comprises 107 amino acids corresponding to positions 54 to 160 (SEQ ID NO: 4);

peptide 4: it comprises 76 amino acids corresponding to positions 161 to 236 (SEQ ID NO: 5);

peptide 5: it comprises 31 amino acids corresponding to positions 237 to 267 (SEQ ID NO: 6);

peptide 6: it comprises 83 amino acids corresponding to positions 268 to 350 (SEQ ID NO: 7);

peptide 7: it comprises 24 amino acids corresponding to positions 351 to 374 (SEQ ID NO: 8);

peptide 8: it comprises 54 amino acids corresponding to positions 375 to 428 (SEQ ID NO: 9);

peptide 9: it comprises 32 amino acids corresponding to positions 429 to 460 (SEQ ID NO: 10);

peptide 10: it comprises 54 amino acids corresponding to positions 461 to 514 (SEQ ID NO: 11);

peptide 11: it comprises 49 amino acids corresponding to positions 515 to 563 (SEQ ID NO: 12);

peptide 12: it comprises 43 amino acids corresponding to positions 564 to 606 (SEQ ID NO: 13);

peptide 13: it comprises 41 amino acids corresponding to positions 607 to 647 (SEQ ID NO: 14).

A subject of the present invention is also a peptide consisting of a fragment of at least 10 consecutive amino acids of a protein defined above in a) or b), particularly a peptide selected from:

the sequences corresponding to peptides 1 to 13 described above, i.e., selected from the sequences SEQ ID NO: 2 to SEQ ID NO: 14, and the sequences SEQ ID NOS: 47 to 53 corresponding to mutants of the hASAP protein in which there is a deletion of the N-terminal portion containing the BRCT domain (Ndel1: residues 304-647 (SEQ ID NO: 48); Ndel2: residues 411-647 (SEQ ID NO: 49); Ndel3: residues 478-647 (SEQ ID NO: 50)) or of the C-terminal portion containing the MAP domain (Cdel1: residues 1 to 477 (SEQ ID NO: 51); Cdel2: residues 1 to 418 (SEQ ID NO: 52); Cdel3: residues 1 to 303 (SEQ ID NO: 53); residues 1 to 421 (SEQ ID NO: 47)).

According to an advantageous embodiment of the invention, said peptide is useful for producing antibodies that specifically recognize a protein as defined above, preferably that recognize the ASAP protein of sequence SEQ ID NO: 1 or SEQ ID NO: 46.

The subject of the invention is thus also monoclonal or polyclonal antibodies, characterized in that they are capable of specifically recognizing a protein according to the invention.

Preferably according to the invention, the antibodies recognize, among MAPs, only and specifically the ASAP protein of sequence SEQ ID NO: 1 or SEQ ID NO: 46.

The antibodies according to the invention are, for example, chimeric antibodies, humanized antibodies, or Fab or F(ab')2 fragments. They may also be in the form of immunoconjugates or of antibodies that have been labeled in order to obtain a detectable and/or quantifiable signal.

Said antibodies can be obtained directly from human serum or from serum of animals immunized with the proteins or the peptides according to the invention.

The specific polyclonal or monoclonal antibodies can be obtained according to techniques well known to those skilled in the art.

A subject of the invention is also the use of the antibodies according to the invention, for detecting and/or purifying a protein according to the invention.

In general, the antibodies according to the invention can be advantageously used for detecting the presence of a normal or mutated protein according to the invention.

In particular, the monoclonal antibodies can be used for detecting these proteins in a biological sample. They thus constitute a means of immunocytochemical or immunohistochemical analysis of the expression of the proteins according to the invention, in particular the protein of sequence SEQ ID NO: 1, on tissue sections. In general for such analyses, the antibodies used are labeled in order to be detectable, for example by immunofluorescent compounds, by means of gold labeling, or in the form of enzymatic immunoconjugates.

They can make it possible in particular to demonstrate abnormal expression of these proteins in the biological tissues or samples, and thus allow the detection of cells exhibiting disturbances in mitotic spindle organization and/or an induction of aberrant and abortive mitoses (plurinuclear cells, monopolar or multipolar spindles) associated with overexpression of the protein according to the invention.

A subject of the invention is also a method for detecting the protein according to the invention, particularly the ASAP protein, in a biological sample, comprising a first step consisting in suitably treating the cells by any appropriate means for making the intracellular medium accessible, a second step consisting in bringing said intracellular medium thus obtained into contact with an antibody according to the invention, and a third step consisting in demonstrating, by any appropriate means, the ASAP protein-antibody complex formed.

This method can also make it possible to measure the level of expression of the protein according to the invention in cells, particularly in cancer cells. The study of the expression of the ASAP protein (overexpression or underexpression) is an element for evaluating the proliferative capacity or the aggressiveness (ability to progress toward cancers with a poor prognosis) of cancer cells.

A subject of the invention is therefore also a method for evaluating, in vitro, the proliferative capacity or aggressiveness of the cancer cells contained in a biological sample, characterized in that it comprises a first step consisting in suitably treating the cells by any appropriate means for making the intracellular medium accessible, a second step consisting in bringing said intracellular medium thus obtained into contact with an antibody according to the invention, a third step consisting in demonstrating and/or measuring, by any appropriate means, the ASAP protein-antibody complex formed, and a fourth step consisting in evaluating the level of transcription of the gene, by comparing the level of ASAP protein-antibody complexes formed with that of a control biological sample selected beforehand. Said control can consist, for example, of a biological sample containing cells having a normal or altered level of proteins, to which said method is applied under the same conditions.

A subject of the invention is also a kit for carrying out any one of the methods described above, comprising:

a) at least one monoclonal or polyclonal antibody according to the invention;

b) the reagents for detecting the ASAP protein-antibody complex produced during the immunoreaction.

According to a particular embodiment of the invention, the kit can optionally comprise reagents required for making the intracellular medium accessible.

The expression "means for making the intracellular medium accessible" is intended to mean any means known to those skilled in the art, for instance cell lysis by enzymatic or chemical processes, or else sonication, membrane permeation, thermal shock.

A subject of the present invention is also an isolated polynucleotide (cDNA or genomic DNA fragment), characterized in that its sequence is selected from the group consisting of:

the sequences encoding a protein or a peptide as defined above, and the sequences complementary to the preceding sequences, that may be sense or antisense.

The invention encompasses the alleles of the asap gene derived from any mammal, and also the polynucleotides of the natural or artificial mutants of the asap gene encoding an ASAP protein, particularly a functional ASAP protein as defined above.

According to an advantageous embodiment of the invention, said polynucleotide encoding an ASAP protein corresponds to a sequence selected from the group consisting of:

the sequence SEQ ID NO: 15, corresponding to the complementary DNA of 2575 nucleotides of the mRNA encoding the human ASAP protein (hASAP);

the sequence SEQ ID NO: 45, corresponding to the complementary DNA of 2767 nucleotides of the mRNA encoding the murine ASAP protein (mASAP);

the genomic DNA fragment of 29750 nucleotides corresponding to the sequence represented in the attached sequence listing under the number SEQ ID NO: 16, corresponding to the human asap gene comprising 14 exons, only 13 of which are translated, the first exon not being translated, contained in the contig AC097467 (length 178204 base pairs) between bases 115117 and 143828 (version v.7.29a3 NCBI/Ensembl of Jul. 12, 2002, www.ensembl.org), moreover located on chromosome 4q32.1 between the anonymous markers D4S1053 and D4S571 (region 161.25 megabases (Mb) to 161.28 Mb).

The sequence SEQ ID NO: 16 is contained in the BAC clone RP11-27G13 (K. Osoegawa et al., (2001) A Bacterial Artificial Chromosome Library for Sequencing the Complete Human Genome, Genome Research, Vol. 11, No. 3, 483-496, March 2001). The sequences contained in the contig AC097467 and in the BAC clone RP11-27G13 were obtained in the context of the human genome sequencing program, and have not up until now been the subject of any precise recognition or characterization making it possible to assign any function to them. Two nucleic acids corresponding to fragments of the polynucleotide isolated by the inventors are listed in the GenBank database under the accession numbers AK024730 and AK024812, along with the ESTs listed under the accession numbers BU198882, BM693711, AW372449, BM021380, BU928828, AL707573, AI885274, AI671785, AA805679, BU619959, BM021126, AL598336, AW976973, BU629726, AI433877, AV51613, BQ372751, AI827535, AI866257, AA843565, R96130, BU684090, BF958121, BQ351941, AW194906, BG203580, BF078132, AW486134, AL600279, AA025538, AL600264, BF170676, BU759494, BB025236, BF214179, AI283076, BE694273, AI266380, BM670854, BM968415, BU503982, BB700612, BE988355, BU058357, BB312934, AW061311, BM537962, BE988356, BB318982, BB311217, BB557152, BB185248, BB557128, BB698742, BB186736, AV345769, BB274293, BB632007, BB617958, AI391312, W18534, BB186581, BB311289, BB312835, AW347411, AA972439, BB263570, AU035125, BB277226, BB274224, BB268445, AW024037, AA025609, BB274174, R96089, BB272238, BB269037, BB385718, BE007324, BB325992, AJ275277, AI414381, BB125476, BB430961, BE932162, BQ121419, BQ121418, BG591509, BF457670, AL897593, AL897592, BM926692, BM538559, BI759567, AL601021, AL598780, AU222540, BG567619, AU166296, BF889835, AU164011, AV656025, BF343454, AW262441, AW237952. These sequences, obtained in the context of a program of mass sequencing of human complementary DNA libraries, are incomplete and have never been either recognized or characterized. In fact, the polynucleotide isolated by the inventors exhibits long deoxyadenosine chains (poly-dA), which explains the difficulties encountered by the inventors in obtaining the complete cDNA using conventional oligodeoxythymidine (oligo-dT) primers, said primers hybridizing randomly with the poly-dA chains. The inventors succeeded in isolating the polynucleotide corresponding to the complete mRNA by repeatedly using the 3' rapid amplification cDNA end (or 3'RACE) technique.

The mRNA, corresponding to the polynucleotide of sequence SEQ ID NO: 15, is specifically expressed in the testes in the form of a polynucleotide approximately 2.9 kilobases long, and in the brain in the form of a polynucleotide approximately 9 kilobases long, that may correspond either to a premessenger or to a high molecular weight isoform.

More precisely, said exons are distributed as follows on said genomic sequence (relative to the numbering of the sequence SEQ ID NO: 16):

exon 1: it comprises 200 base pairs corresponding to positions 101 to 300 (SEQ ID NO: 17);

exon 2: it comprises 139 base pairs corresponding to positions 1157 to 1295 (SEQ ID NO: 18);

exon 3: it comprises 85 base pairs corresponding to positions 2050 to 2134 (SEQ ID NO: 19);

exon 4: it comprises 321 base pairs corresponding to positions 3615 to 3935 (SEQ ID NO: 20);

exon 5: it comprises 227 base pairs corresponding to positions 8259 to 8485 (SEQ ID NO: 21);

exon 6: it comprises 94 base pairs corresponding to positions 14930 to 15023 (SEQ ID NO: 22);

exon 7: it comprises 248 base pairs corresponding to positions 16715 to 16962 (SEQ ID NO: 23);

exon 8: it comprises 71 base pairs corresponding to positions 19552 to 19622 (SEQ ID NO: 24);

exon 9: it comprises 169 base pairs corresponding to positions 21187 to 21355 (SEQ ID NO: 25);

exon 10: it comprises 90 base pairs corresponding to positions 21911 to 22000 (SEQ ID NO: 26);

exon 11: it comprises 162 base pairs corresponding to positions 23731 to 23892 (SEQ ID NO: 27);

exon 12: it comprises 146 base pairs corresponding to positions 24014 to 24159 (SEQ ID NO: 28);

exon 13: it comprises 133 base pairs corresponding to positions 24343 to 24475 (SEQ ID NO: 29);

exon 14: it comprises 485 base pairs corresponding to positions 29166 to 29650 (SEQ ID NO: 30).

A subject of the invention is also:

a fragment of any one of the polynucleotides according to the invention, of at least 15 to 1500 consecutive nucleotides, with the exclusion of the sequences listed under the accession numbers AK024730 and AK024812 and of the ESTs listed under the accession numbers BU198882, BM693711, AW372449, BM021380, BU928828, AL707573, AI885274, AI671785. AA805679, BU619959, BM021126, AL598336, AW976973, BU629726, AI433877, AV751613, BQ372751, AI827535, AI866257, AA843565, R96130, BU684090, BF958121, BQ351941, AW194906, BG203580, BF078132, AW486134, AL600279, AA025538, AL600264, BF170676, BU759494, BB025236, BF214179, AI283076, BE694273, AI266380, BM670854, AA968415, BU503982, BB700612, BE988355, BU058357, BB312934, AW061311, BM537962, BE988356, BB318982, BB311217, BB557152, BB185248, BB557128, BB698742, BB186736, AV345769, BB274293, BB632007, BB617958, AI391312, W18534, BB186581, BB311289, BB312835, AW347411, AA972439, BB263570, AU035125, BB277226, BB274224, BB268445, AW024037, AA025609, BB274174, R96089, BB272238, BB269037, BB385718, BE007324, BB325992, AJ275277, AI414381, BB125476, BB430961, BE232162, BQ121419, BQ121418, BG591509, BF457670, AL897593, AL897592, BM926692, BM538559, BI759567, AL601021, AL598780, AU222540, BG567619, AU166296, BF889835, AU164011, AV656025, BF343454, AW262441, AW237952 in the GenBank database, particularly a fragment selected from the sequences corresponding to the exons, i.e. selected from the sequences SEQ ID NO: 16 to SEQ ID NO: 30;

a nucleic acid exhibiting a percentage identity of at least 80%, preferably of at least 90%, with one of the polynucleotides according to the invention.

The definition of the identity of a sequence given above for the proteins applies by analogy to the nucleic acid molecules.

Included in a polynucleotide exhibiting a percentage identity of at least 80%, preferably of at least 90%, according to the invention, are the polynucleotides that are variants of the sequences SEQ ID NOS: 15 and 45, i.e. all the polynucleotides corresponding to allelic variants, i.e. to individual variations of the sequences SEQ ID NOS: 15 and 45. These natural variant sequences correspond to polymorphisms present in mammals, in particular in human beings, and especially to polymorphisms that may result in the occurrence of a pathology.

The term "variant polynucleotide" is also intended to denote any RNA or cDNA resulting from a mutation and/or from a variation of a splice site of the genomic sequence which has an mRNA whose complementary DNA is the polynucleotide of sequence SEQ ID NO: 15 or SEQ ID NO: 45.

Preferably, the present invention relates to the polynucleotides or the fragments that are variants of the sequences SEQ ID NOS: 15 and 45, particularly those in which the mutations result in a modification of the amino acid sequence of the proteins of sequence SEQ ID NO: 1 and SEQ ID NO: 46.

The polynucleotides according to the invention can be isolated from cells, particularly from the cells of the testes or the brain, or from cellular DNA libraries. They can also be obtained by means of a polymerase chain reaction (PCR) carried out on the total DNA of the cells or else by RT-PCR carried out on the total RNA of the cells, or by chemical synthesis.

The polynucleotides according to the invention, particularly the fragments of any one of the polynucleotides according to the invention, and the sequences listed under the accession numbers AK024730 and AK024812 and the ESTs listed under the accession numbers BU198882, BM693711, AW372449, BM021380, BU928828, AL707573, AI885274, AI671785, AA805679, BU619959, BM021126, AL598336, AW976973, BU629726, AI433877, AV751613, BQ372751, AL327535, AI866257, AI843565, R96130, BU684090, BF958121, BQ351941, AW194906, BG203580, BF078132, AW486134, AL600279, AA025538, AL600264, BF170676, BU759494, BB025236, BF214179, AI283076, BE694273, AI266380, BM670854, AA968415, BU503982, BB700612, BE988355, BU058357, BB312934, AW061311, BM537962, BE988356, BB318982, BB311217, BB557152, BB185248, BB557128, BB698742, BB186736, AV345769, BB274293, BB632007, BB617958, AI391312, W18534, BB186581, BB311289, BB312835, AW347411, AA972439, BB263570, AW35125, BB277226. BB274224, BB268445, AW024037, AA025609, BB274174, R96089, BB272238, BB269037, BB385718, BE007324, BB325992, AJ275277, AI414381, BB125476, BB430961, BE232162, BQ121419, BQ121418, BG591509, BF457670, AL897593, AL897592, BM926692, BM538559, BI759567, AL601021, AL598780, AU222540, BG567619, AU166296, BF889835, AU164011, AV656025, BF343454, AW262441, AW237952 in the GenBank database, or their fragments, can in particular be used as probes or as primers for detecting/amplifying polynucleotides (RNA or genomic DNA) corresponding to the polynucleotide according to the invention, particularly in other organisms.

The transcripts of the asap gene are, for example, preferably demonstrated using probes selected from the group consisting of the sequences SEQ ID NO: 15, SEQ ID NO: 45, and SEQ ID NO: 17 to SEQ ID NO: 44, or using an EST as defined above, or amplified by RT-PCR using primers selected from the group consisting of the sequences SEQ ID NOS: 31 to 43.

The polynucleotide according to the invention can make it possible to diagnose a pathological state or a genetic disease involving a dysfunction of the asap gene, and to screen for substances capable of modulating (activating or inhibiting) the transcription of said gene.

A subject of the invention is also the polynucleotides that can be obtained by amplification using the primers according to the invention.

The probes and primers according to the invention can be directly or indirectly labeled with a radioactive or non-radioactive compound by methods well known to those skilled in the art, in order to obtain a detectable and/or quantifiable signal.

The labeling of the probes according to the invention is carried out with radioactive elements or with non-radioactive molecules. Among the radioactive isotopes used, mention may be made of $^{32}P$, $^{33}P$, $^{35}H$, $^{3}H$ or $^{125}I$. The non-radioactive entities are selected from ligands such as biotin, avidin, streptavidin or digoxigenin, haptens, dyes, and luminescent agents such as radioluminescent, chemoluminescent, bioluminescent, fluorescent or phosphorescent agents.

The polynucleotides according to the invention can thus be used as a primer and/or a probe in methods using in particular the PCR (polymerase chain reaction) technique (U.S. Pat. No. 4,683,202). Other techniques for amplifying the target nucleic acid can advantageously be used as an alternative to PCR. A large number of methods currently exist that allow this amplification, for instance the SDA (Strand Displacement Amplification) technique, the TAS (Transcription-based Amplification System) technique, the 3SR (Self-sustained Sequence Replication) technique, the NASBA (Nucleic Acid Sequence Based Amplification) technique, the TMA (Transcription Mediated Amplification) technique, the LCR (Ligase Chain Reaction) technique, the RCR (Repair Chain Reaction) technique, the CPR (Cycling Probe Reaction) technique, or the Q-beta-replicase amplification technique. Mention may also be made of PCR-SSCP, which makes it possible to detect point mutations.

These techniques are of course entirely known to those skilled in the art.

As probes or as primers, the various polynucleotides according to the invention can make it possible either to determine the transcription profile of the corresponding asap gene or any possible alteration of this profile in a biological sample, or to demonstrate the corresponding gene in other species, allelic variants of this gene or any possible functional alteration of this gene (substantial change in the activity of the protein encoded by said gene) resulting from a mutation (insertion, deletion or substitution) of one or more nucleotides in at least one exon of said gene. Such mutations include in particular deletions, insertions or non-conservative substitutions in codons corresponding to amino acid residues located in a domain that is essential for the biological activity of the protein.

Thus, a subject of the invention is a method for determining the transcription profile of the gene corresponding to the polynucleotide according to the invention, or an alteration in said profile, in a biological sample, comprising a first step consisting in obtaining, by any appropriate means, the total RNA from the biological sample, a second step consisting in bringing said RNA into contact with a probe according to the invention, labeled beforehand, under conventional conditions for hybridization between the RNAs and the probe, and a third step consisting in revealing, by any appropriate means, the hybrids formed.

The expression "conventional conditions for hybridization" is intended to mean those described in J. Sambrook, D. W. Russell (2000) Cold Spring Harbor Laboratory Press.

According to one embodiment of said method, the second step can be a step consisting of reverse transcription and amplification of the transcripts, carried out using a pair of primers as described above, and the third step can be a step consisting in revealing, by any appropriate means, the amplified nucleic acids formed.

Said method for determining the transcription profile of the gene can also comprise a step consisting in evaluating the level of transcription of the gene by comparison with a control sample selected beforehand. Said control may, for example, consist of a biological sample exhibiting normal or altered transcription of the gene corresponding to the polynucleotide according to the invention, to which said method for determining the transcription profile of the gene is applied under the same conditions.

A subject of the invention is also a method for demonstrating, in other species, the gene corresponding to the polynucleotide according to the invention or the allelic variants of said gene, or a functional alteration of this gene, in a biological sample, comprising a first step consisting in obtaining, by any appropriate means, the DNA from the cells of a biological sample, a second step consisting in bringing said DNA into contact with a probe according to the invention, labeled beforehand, under conventional conditions for hybridization between the DNAs and the probe, and a third step consisting in revealing, by any appropriate means, the hybrids formed.

According to one embodiment of said method, the second step can be an amplification step carried out using a pair of primers as described above, and the third step can be a step consisting in revealing, by any appropriate means, the amplified nucleic acids formed. The method can optionally comprise a fourth step consisting in isolating and sequencing the nucleic acids demonstrated.

A subject of the invention is also a kit of reagents for carrying out the methods described above, comprising:
a) at least one probe or one pair of primers according to the invention;
b) the reagents required for carrying out a conventional hybridization reaction between said probe or said primers and the nucleic acid of the biological sample;
c) the reagents required for carrying out an amplification reaction;
d) the reagents required for detecting and/or assaying the hybrid formed between said probe and the nucleic acid of the biological sample or the amplified nucleic acids formed.

Such a kit can also contain positive or negative controls in order to ensure the quality of the results obtained. It can also contain the reagents required for purifying the nucleic acids from the biological sample.

The polynucleotide of the invention or one of its fragments, and also the ESTs described above or their fragments, can be used to develop cell or animal models that do not express the ASAP protein, by knocking out the ASAP gene by means of the Si RNA method (small interfering RNA; M. McManus and P. Sharp, Nature Reviews Genetics, 3, 737-747, 2002; V. Brondani, F. Kolb, E. Billy, M/S, 6-7, 665-667, 2002) using oligonucleotides derived from their sequences.

A subject of the invention is also a cloning and/or expression vector into which the polynucleotide according to the invention is inserted.

Such a vector can contain the elements required for the expression and, optionally, the secretion of the protein in a host cell.

Said vectors preferably comprise: a promoter, translation initiation and termination signals, and also regions suitable for regulating the transcription. It should be possible for them to be maintained stably in the cell and they can optionally comprise sequences encoding specific signals specifying the secretion of the translated protein, for instance a strong ubiquitous promoter or a promoter that is selective for a particular cell and/or tissue type. These various control sequences are chosen according to the cellular host used.

The polynucleotide according to the invention can be inserted into vectors that replicate autonomously in the chosen host or vectors that are integrative with the chosen host.

Among the autonomously replicating systems, use is preferably made, according to the host cell, of systems of the plasmid or viral type. The viral vectors can in particular be adenoviruses, retroviruses, lentiviruses, poxviruses or herpesviruses. Those skilled in the art are aware of the technology that can be used for each of these systems.

When integration of the sequence into the chromosomes of the host cell is desired, use may be made, for example, of systems of the plasmid or viral type; such viruses are, for example, retroviruses or adeno-associated viruses (AAVs).

Among the non-viral vectors, preference is given to naked polynucleotides such as naked DNA or naked RNA, bacterial artificial chromosomes (BACs), yeast artificial chromosomes (YACs) for expression in yeast, mouse artificial chromosomes (MACs) for expression in murine cells, and preferably human artificial chromosomes (HACs) for expression in human cells.

Such vectors are prepared according to the methods commonly used by those skilled in the art, and the recombinant vectors resulting therefrom can be introduced into the appropriate host by standard methods, for instance lipofection, electroporation, thermal shock, transformation after chemical membrane permeabilization, cell fusion.

A subject of the invention is also the transformed host cells, in particular the eukaryotic and prokaryotic cells, into which at least one polynucleotide or one fragment according to the invention or at least one vector according to the invention has been introduced.

Among the cells that can be used for the purposes of the present invention, mention may be made of bacterial cells, yeast cells, animal cells, in particular mammalian cells, or else plant cells. Mention may also be made of insect cells in which methods employing for example baculoviruses can be used.

A subject of the invention is also the nonhuman transgenic organisms, such as the transgenic animals or plants, in which all or some of the cells contain the polynucleotide according to the invention or the vector according to the invention, in free or integrated form.

Preferably according to the invention, the nonhuman transgenic organisms are those carrying cells containing a polynucleotide according to the invention, that is nonfunctional or carrying a mutation.

According to the invention, the transgenic animals are preferably mammals, except for humans, more preferably rodents, in particular mice or rats.

The transgenic animals can be obtained by any conventional method known to those skilled in the art, for instance by homologous recombination on embryonic stem cells, transfer of these stem cells to embryos, selection of the chimeras affected in the reproductive lines, and growth of such chimeras.

The transformed host cells, the transgenic animals or the transgenic plants according to the invention can thus express or overexpress the gene encoding the protein according to the invention, or their homologous gene, or express said gene into which a mutation is introduced.

The testicular or brain cells, the transformed host cells or the transgenic organisms according to the invention can be used for preparing the protein according to the invention.

The protein according to the invention, particularly the native ASAP protein, can be purified according to techniques known to those skilled in the art. Thus, the protein can be purified from cell lysates and extracts, from the culture medium supernatant, by methods used individually or in combination, such as fractionation, chromatography methods, particularly affinity chromatography methods, immunoaffinity techniques using specific monoclonal or polyclonal antibodies, etc.

The subject of the invention is also a method for preparing the ASAP protein, characterized in that cells expressing the protein or transformed cells according to the present invention, in particular mammalian cells or the cells of transgenic organisms according to the invention, are cultured under conditions that allow the expression of said protein, and in that said protein is purified.

As a purification technique, mention may be made, for example, of affinity chromatography on glutathionesepharose (or agarose) as described in J Sambrook & D W Russell (2000, Cold Spring Harbor Laboratory Press).

A subject of the invention is also a protein, characterized in that it can be obtained by means of any one of the methods of preparation described above.

A subject of the invention is also a method for screening for a substance capable of interacting in vitro, directly or indirectly, with the polynucleotide or the protein according to the invention, characterized in that:

in a first step, the substance to be tested and the polynucleotide or the protein according to the invention are brought into contact, and in a second step, the complex formed between said substance and the polynucleotide or the protein according to the invention is detected by any appropriate means.

A subject of the present invention is also a method for screening for a substance capable of modulating (activating or inhibiting) the activity of the ASAP protein, characterized in that:

in a first step, cells of a biological sample expressing the ASAP protein are brought into contact with a substance to be tested, in a second step, the effect of said substance on the activity of said ASAP protein is measured by any appropriate means, and in a third step, substances capable of modulating said activity are selected.

For the purpose of the present invention, the expression "activity of the ASAP protein" is intended to mean both the expression of the ASAP protein or of the corresponding transcripts (mRNA), and the biological activity of said ASAP protein, for instance its effect on the organization of the mitotic spindle or the induction of aberrant or abortive mitoses.

The detection of the complex formed between said substance and the polynucleotide or the protein, or the measurement of the effect of said substance on the activity of said ASAP protein, can be carried out by conventional techniques of mRNA or protein analysis that are known in themselves; by way of nonlimiting example, mention may be made of the following techniques: RT-PCR, Northern blotting, Western blotting, RIA, ELISA, immunoprecipitation, immunocytochemical or immunohistochemical analysis techniques.

Advantageously, said measurement is carried out using the probes, the primers or the antibodies as defined above.

Such substances can be biological macromolecules such as, for example, a nucleic acid, a lipid, a sugar, a protein, a peptide, a protein-lipid, protein-sugar, peptide-lipid or peptide-sugar hybrid compound, a protein or a peptide to which have been added chemical branches or else chemical molecules.

The subject of the invention is also the polynucleotide, the protein, the antibodies, the vectors or the transformed cells according to the invention, used as medicinal products.

As indicated above, the overexpression of the protein according to the invention blocks cell division and, consequently, cell proliferation. This makes it an excellent candidate for use as an anti-mitotic agent, that can be used for example in the treatment of cancer-related pathologies.

Thus, a subject of the invention is also the use of the polynucleotide, of a vector or of the protein according to the invention, in the preparation of an anti-mitotic medicinal product.

Similarly, as is also indicated above, the overexpression of the protein according to the invention disturbs the organization of the mitotic spindle and induces aberrant and abortive mitoses (plurinuclear cells, monopolar or multipolar spindles).

Thus, a subject of the invention is also the use of an antisense polynucleotide or of an antisense fragment, of an antibody, or of a vector containing an antisense oligonucleotide, according to the invention, capable of inhibiting the expression of the polynucleotide or of the protein according to the invention, in the preparation of a medicinal product intended for the treatment of pathologies associated with disturbances in mitotic spindle organization and/or induction of aberrant and abortive mitoses (plurinuclear cells, monopolar or multipolar spindles) associated with overexpression of the protein according to the invention.

BRIEF DESCRIPTION OF THR DRAWINGS

Besides the above provisions, the invention also comprises other provisions that will emerge from the following description, which refers to examples of implementation of the invention and also to the attached drawings, in which.

(A) by agarose gel electrophoresis of the RT-PCR products obtained with primers corresponding to the mouse polynucleotide, which is the ortholog of the polynucleotide SEQ ID NO: 15, using various mouse tissues;

(B) after transfer of the gel, after electrophoresis, onto a membrane and hybridization with an internal MASAP probe.

Figure 4:
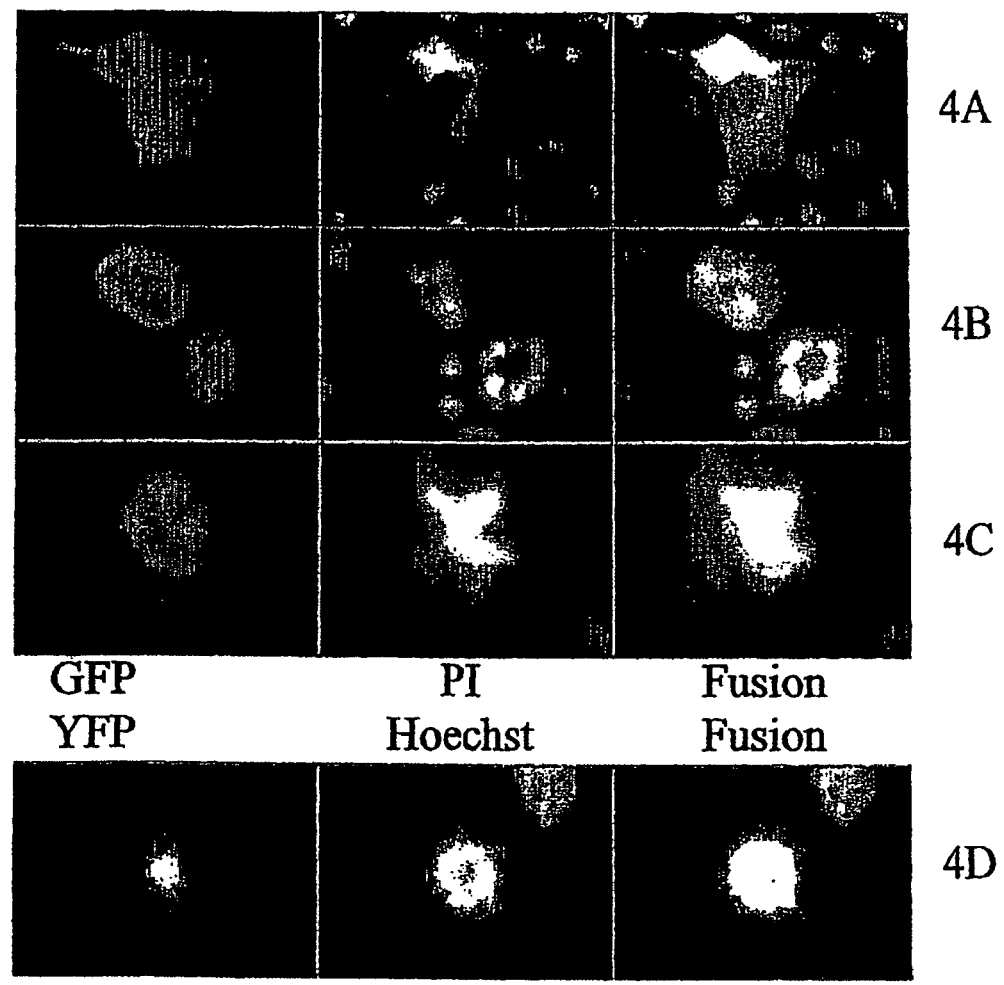

FIG. 4 represents the cellular localization of the hASAP protein coupled to the green fluorescent protein (GFP) in the 3' position or the yellow fluorescent protein (YFP) in the 5' position, or to an MYC tag on the N-terminal side (fusion column).

The nuclei are stained with propidium iodide or with Hoechst 33286 (4A: 63× objective; 4B, 4C and 4D: 100× objective).

Figure 5:
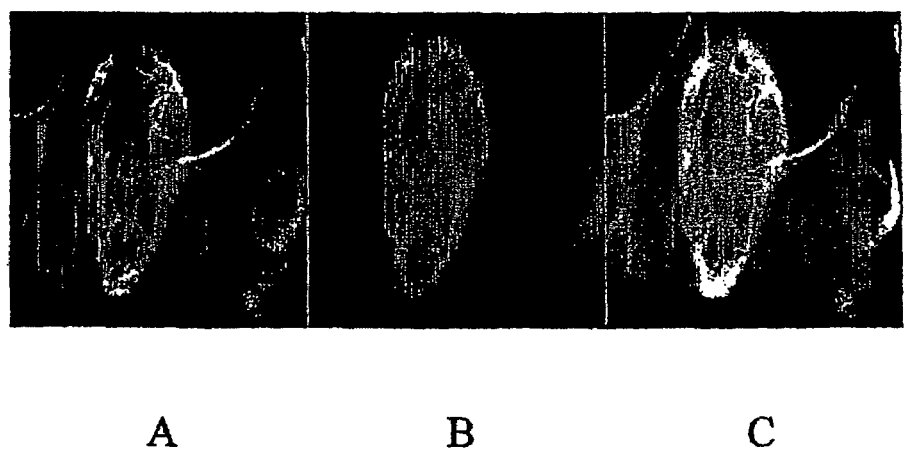

FIG. 5 shows the colocalization of the human ASAP protein with alpha-tubulin. FIG. 5A: cellular localization of alpha-tubulin, FIG. 5B: localization of the ASAP protein, FIG. 5C: superimposition of the 2 images showing the colocalization of the 2 proteins.

The following examples illustrate the invention but in no way limit it.

EXAMPLE 1

Construction of the Complete ASAP Coding Sequence

The complete sequence of the cDNA of the ASAP protein is amplified from 2 overlapping fragments:

```
a fragment A amplified by PCR from the clone
AI885274 with the primers:
                                    (SEQ ID NO: 31)
constFIS-1F (5'-ATGTCTGATGAAGTTTTTAGCACC-3')
and (SEQ ID NO: 32)
constFIS-2R (5'-AGGCCTCAAATGATGCTAATGC-3';

a fragment B amplified from the clone AI671785
with the primers:
                                    (SEQ ID NO: 33)
constFIS-2F (5'-ATCATTTGAGGCCTGGAAGGC-3')
and (SEQ ID NO: 34)
constFIS-1R (5'-AAACACTTTTGCGAACACAGTTC-3').
```

Next, in order to obtain a single PCR product corresponding to the complete sequence of the cDNA of the ASAP protein, that can be used for the function experiments, 0.5 μl of the products of each of the two PCR reactions (fragment A and B) are hybridized together at 25° C. and then amplified with the primers constFIS-1F and constFIS-2F. This PCR product is subcloned into the vector PCR4 according to the producer's (Invitrogen) recommendations, and verified by sequencing.

The major difficulties encountered lay in the determination, in silico, of the complete ASAP coding sequence and its reconstruction in vitro. In particular, the choice of the primers and of the various PCRs of the 3' region were tricky due to the sequence being rich in polyA.

EXAMPLE 2

Bioinformatic Analysis

Figure 1:
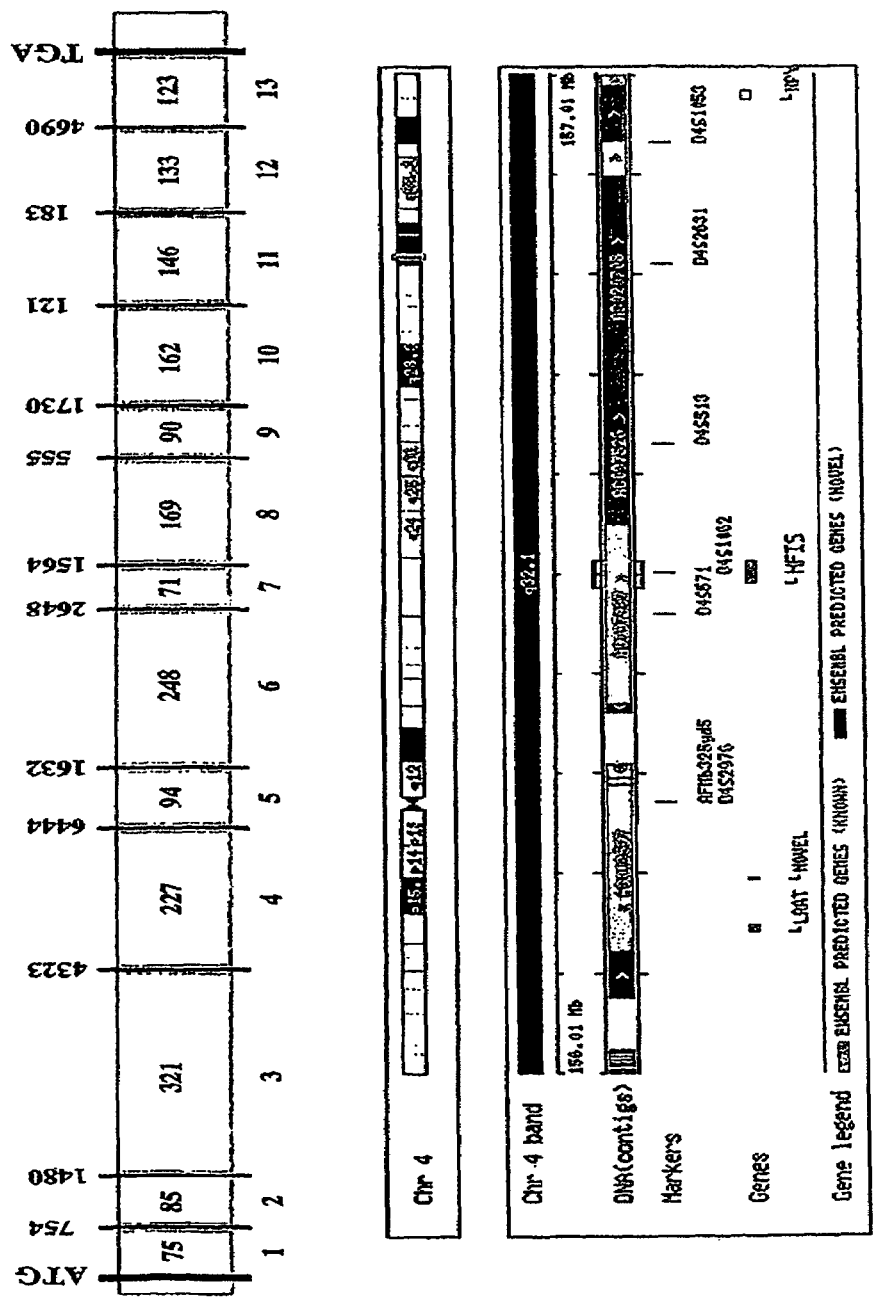
FIG. 1 represents the chromosomal localization and the structure of the human asap gene.

FIG. 1 represents the chromosomal localization and the structure of the human asap gene.

The complete organization of the asap gene and its chromosomal localization were obtained by comparing the sequence of the cDNA obtained in example 1, with the sequence of the human genome, using the Wellcome Trust Sanger Institute programs and more particularly the BLAST search program.

The human asap gene consists of 29750 nucleotides comprising 14 exons, only 13 of which are translated, the first exon not being translated. The size of the exons ranges from 71 to 321 base pairs. The sequence of the gene is contained in the contig AC097467 (length 178204 base pairs) between bases 115117 and 143828 (version v.7.29a3 NCBI/Ensembl of Jul. 12, 2002, and is, moreover, located on chromosome 4q32.1 between the anonymous markers D4S1053 and D4S571 (region 161.25 megabases (Mb) to 161.28 Mb). The sequence of the gene is physically contained in the BAC clone RP11-27G13.

Two nucleic acids corresponding to fragments of the polynucleotide isolated by the inventors are listed in the GenBank database under the accession numbers AK024730 and AK024812, along with the ESTs listed under the accession numbers BU198882, BM693711, AW372449, BM021380, BU928828, AL707573, AI885274, AI671785, AA805679, BU619959, BM021126, AL598336, AW976973, BU629726, AI433877, AV751613, BQ372751, AI827535, AI866257, AA843565, R96130, BU684090, BF958121, BQ351941, AW194906, BG203580, BF078132, AW486134, AL600279, AA025538, AL600264, BF170676, BU759494, BB025236, BF214179, AI283076, BE694273, AI266380, BM670854, AA968415, BU503982, BB700612, BE988355, BU058357, BB312934, AW061311, BM537962, BE988356, BB318982, BB311217, BB557152, BB185248, BB557128, BB698742, BB186736, AV345769, BB274293, BB632007, BB617958, AI391312, W18534, BB186581, BB311289, BB312835, AW347411, AA972439, BB263570, AU035125, BB277226, BB274224, B8268445, AW024037, AA025609, BB274174, R96089, BB272238, BB269037, BB385718, BE007324, BB325992, AJ275277, AI414381, BB125476, BB430961, BB232162, BQ121419, BQ121418, BG591509, BF457670, AL897593, AL897592, BM926692, BM538559, BI759567, AL601021, AL598780, AU222540, BG567619, AU166296, BF889835, AU164011, AV656025, BF343454, AW262441, AW237952.

These sequences, obtained in the context of a program of mass sequencing of human complementary DNA libraries, are incomplete and have never been either recognized or characterized.

The protein sequence was compared to the databank sequences using the PSI-BLAST programs of the NCBI. Consensus protein motifs were sought using the DART programs of the NCBI and the SMART program of ExPASy-Tools, the parameters of which make is possible to detect motifs with weak homology. The ASAP protein exhibits a sequence identity of 23% over the C-terminal third with a microtubule-associated protein (MAP 1A, for microtubule-associated protein 1A). Moreover, the search for conserved motifs (DART or SMART) reveals domains of caldesmon type (N.B. Gusev, Biochemistry, 10 1112-1121, 2000) and ERM type (ezrin/radixin/moesin) (Louvet-Vallet, S., Biol. Cells. 274: 305-316, 2000), which are proteins that are also considered to be MAPs, with identities of approximately 20%. It also has a BRCT domain (breast cancer carboxy-terminal domains; P. Bork et al., J. FASEB, 11, 6876 (1997)) between positions 65 and 303.

The ASAP protein has coiled-coil domains essentially included in its C-terminal portion between, firstly, amino acids 297 and 327 and, secondly, amino acids 477 and 628, indicating either that the protein oligomerizes, or that it interacts with other proteins.

Computer analysis of the protein using the programs accessible on the Internet site reveals that it lacks β-sheets and is very rich in α-helices, in particular in the region between amino acids 420-620, which is almost exclusively made up of α-helices.

Computer analysis of the protein using the programs accessible on the Internet site (http://npsa-bil.ibcp.fr/cgi-bin/np-sa_automat.pl?page=/NPSA/npsa_se-cons.html) reveals that it lacks β-sheets and is very rich in α-helices, in particular in the region between amino acids 420-620, which is almost exclusively made up of α-helices.

These elements make it possible to consider that the ASAP protein is a novel MAP.

EXAMPLE 3

Tissue Expression a) Analysis by Northern blotting

Preparation of Radioactive Probes:

The DNAs to be radiolabeled are isolated on a low melting point (LMP) gel according to the technique described by S. Rouquier et al. (Genomics, 17, 330-340, (1993)). Approximately 100 ng of DNA thus isolated are labeled by random priming (Klenow fragment, Proméga) in the presence of [α$^{32}$P dCTP] (Amersham) according to the technique described in A. P. Feinberg & B. Vogelstein (Anal. Biochem., 132, 6-13, (1983)). These probes are purified on Sephadex G-50 columns according to the technique described in J Sambrook & D W Russell (2000, Cold Spring Harbor Laboratory Press). The hybridizations are carried out overnight in the presence of 2·10$^6$ Cpm/ml of denatured radioactive probe.

a.1) Hybridization

Two Northern blotting membranes from the company Clontech (Human MTN Blot and Human MTN Blot II, Ref. 7760-1 and 7759-1) containing human mRNAs from various tissues were hybridized with the complete hASAP cDNA labeled as described above. The membrane was hybridized in the presence of formamide at 42° C., according to the Clontech protocol. A membrane hybridization control was carried out with an actin probe. The membrane was rinsed twice at high stringency in 0.1×SSC/0.1% SDS at a temperature of 42° C., for 15 minutes. The membranes were then analyzed by autoradiography or on a PhosphorImager.

The tissues tested were: spleen, thymus, prostate, testes, ovary, small intestine, colon, blood leukocytes, heart, brain, placenta, lung, liver, skeletal muscle, kidney and pancreas.

a.2) Results

Figure 2:
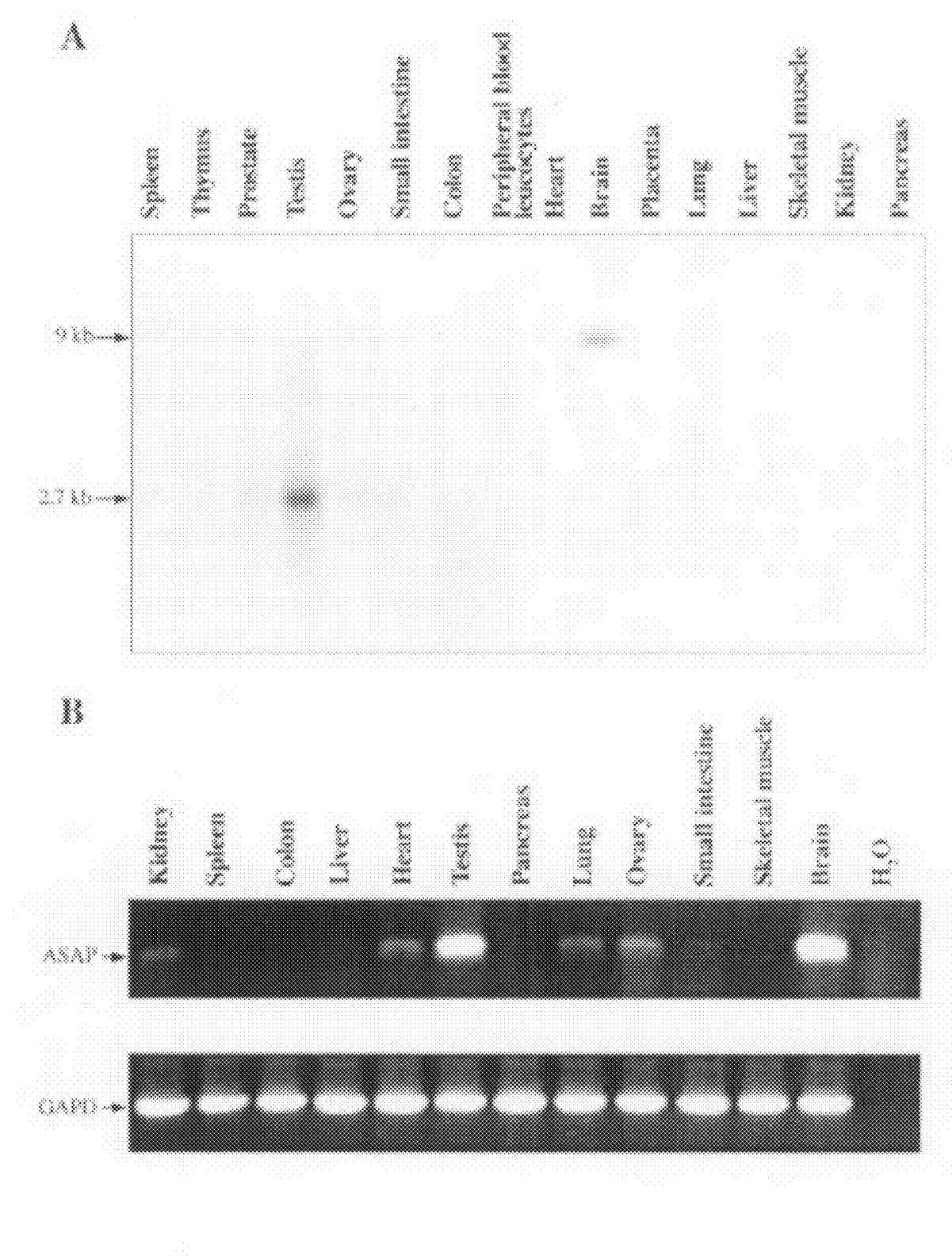
FIG. 2 represents the signals obtained by Northern blotting on various human tissues after hybridization with an hASAP probe.

FIG. 2 illustrates these results.

Two signals were detected:
- a signal in the testes at approximately 2.6 kb, which corresponds to the size of the mRNA;
- a signal in the brain, but at a high molecular weight (9 kb), which corresponds either to a premessenger, or to a high molecular weight isoform.

b) Analysis by RT-PCR

This analysis was carried out on total RNA from various mouse tissues, namely brain, heart, colon, liver, small intestine, skeletal muscle, pancreas, lung, kidney, spleen and testes.

b.1) Obtaining the Mouse Orthologous cDNA

The total RNA from cells of various mouse tissues was extracted with the "mammalian total RNA kit" from the company Sigma. The RNAs were reverse-transcribed with the Superscript II kit from the company Invitrogen according to the conditions recommended by the supplier, and using oligodT primers. The products obtained were verified by 1% agarose gel electrophoresis. 1 μl of each sample thus obtained was, in turn, amplified by PCR (25 μl of reaction medium, 30 cycles (94° C. for 15 seconds, 55° C. for 30 seconds, 72° C. for 30 seconds)) with primers specific for the mouse asap gene (mFIS-1F, 5'-ACA ACG AAT AAC AGA GTG TCC-3' (SEQ ID NO: 35) and mFIS-2R, 5'-ACT CCT GAT AAA CAG CTG CC-3' (SEQ ID NO: 36)).

The amplified products obtained were analyzed by electrophoresis on a 1% agarose gel, stained with ethydium bromide, and their size was compared with a size marker loaded onto the gel in parallel.

After electrophoresis, the amplified products obtained were transferred by capillarity onto a charged nylon membrane, in a 1.5 M NaCl/0.5 M NaOH buffer, according to the Southern technique (alkaline transfer). The membrane was then hybridized with a radiolabeled mASAP probe (SEQ ID NO: 44) generated by amplification of the sequence contained in the mouse clone AW06131 selected after comparison of the human ASAP sequence in the databanks (GenBank) (http://expression.gnf.org/-promoter/tissue/images/41739_s_at.png).

The amplification was carried out by PCR (conditions as described above, in which the reaction volume was 50 μl and the cold dCTP was at a concentration of 10 μM supplemented with 50 μCi of α-P32-dCTP at 3000 Ci/mmole), using the primers mFIS-1F (SEQ ID NO: 35) and mFis-2R (SEQ ID NO: 36). The hybridizations were carried out at 65° C. (in 6×SSC buffer/0.5% SDS/5× Denhardt's solution). The membrane was rinsed at high stringency (0.1×SSC/0.1% SDS), and then analyzed by autoradiography or on a PhosphorImager.

b.2) Results

Figure 3:
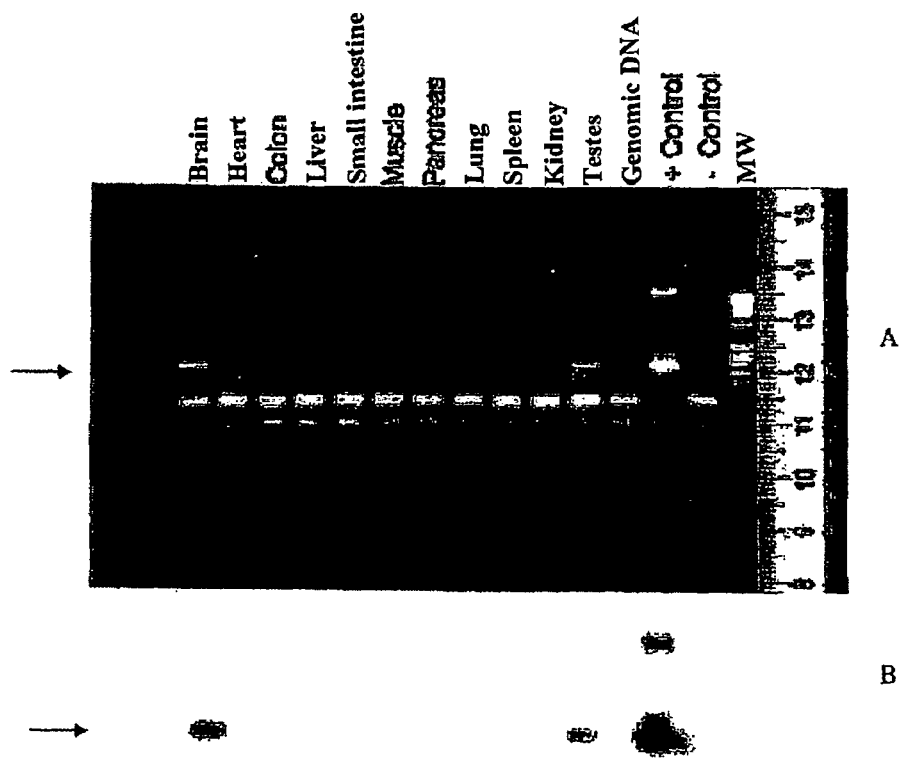
FIG. 3 represents the results obtained.

FIG. 3 illustrates these results.

It is noted that a major signal is obtained in the testes and the brain, which is clearly visible on the gel (FIG. 3A).

After transfer of the gel and hybridization with an internal probe, it is noted that a very weak signal is detected in the other tissues (FIG. 3B).

Consequently, the mRNA encoding the mASAP protein is mainly expressed in the testes and the brain. The complete mouse cDNA, amplified by RT-PCR from the mouse testicular RNA, corresponds to the sequence SEQ ID NO: 45 and the corresponding protein (mASAP) corresponds to the sequence SEQ ID NO: 46.

EXAMPLE 4

Cellular Localization a) Subcloning of the hASAP cDNA in a Eukaryotic Expression Vector The hASAP cDNA obtained in example 1 was inserted into three expression vectors:
1—into pEAK10-EGFP in phase with the green fluorescent protein (GFP) fused in the C-terminal position (vector 1) (pEAK10, vector from Edge Biosystems (distributed by Q.BIOgene, Illkirch in France) into which the EGFP protein (enhanced green fluorescent protein) has been introduced according to the reference I. Gaillard et al., Eur. J. Neurosci, 15 409-418, 2002);
2—into pEYFP-C1 in phase with the yellow fluorescent protein (YFP) fused on the N-terminal side (vector 2) (distributed by BD Biosciences Clontech);

3—into GLOMYC3-1 comprising an MYC tag on the N-terminal side (vector 3), a vector derived from the vector pcDNA3.1 (Invitrogen), into which a 5' untranslated region (5'UTR) and an MYC tag have been inserted at the HindIII-BamHI sites, and the 3'UTR region of globin (SpeI-XbaI fragment) has been inserted in the XbaI site.

The hASAP cDNA was amplified from its initial cloning vector (pCR4-TOPO) by PCR using the pfu Turbo high-fidelity polymerase, with primers that amplify the cDNA between the starting methionine and the last amino acid. The amplified products obtained were subcloned into the three vectors.

Cloning in PEAK-GFP. Preparation of the DNA insert by PCR [94° C. 2 min; (94° C. 15 sec; 58° C. 30 sec; 72° C. 1 min 30 sec) 30 cycles; 72° C. 3 min], using the primers

```
                                       (SEQ ID NO: 37)
hFIS-Exp1F (5'-GCCACCATGTCTGATGAAGTTTTTAGCAC-3)
and (SEQ ID NO: 38)
hFIS-Exp1R (5'-GAAACACTTTTGCGAACACAGTTC-3').
```

The vector was cleaved with EcoRV and dephosphorylated: 10 ng of vector were used for the ligation with the DNA insert. The PCR product was phosphorylated and then purified on a high PURE PCR kit (Roche): 100 ng of insert were used for the ligation [12 h at 16° C. in a final volume of 10 µl (Biolabs ligase), according to standard conditions (Sambrook and Russell)].

Cloning in Glomyc: Preparation of the DNA insert by PCR [94° C. 2 min; (94° C. 15 sec; 60° C. 30 sec; 72° C. 1 min 30 sec) 30 cycles; 72° C. 3 min], using the primers:

```
Glomyc-FIS1F:
                                       (SEQ ID NO: 39)
(5'-TAATGTCTGATGAAGTTTTTAGCACC-3')
and Glomyc-FIS1R:
                                       (SEQ ID NO: 40)
(5'-TCAAAACACTTTTGCGAACACAGTTC-3').
```

Cloning conditions were identical to those described for the cloning in PEAK-GFP.

Cloning in YFP: Preparation of the DNA insert: same conditions as for Glomyc, using the primers:

```
                                       (SEQ ID NO: 41)
YFP-FIS1F (5'-AATGTCTGATGAAGTTTTTAGCACC-3')
and (SEQ ID NO: 40)
Glomyc-FIS1R (cf. above).
```

Cloning conditions were identical to those described for the cloning in PEAK-GFP, the vector having been cleaved beforehand with Sma1.

The recombinants were analyzed by PCR using a primer for the vector and an internal primer.

PEAK-GFP: annealing at 58° C., extension 45 sec at 72° C., and standard conditions for the rest. Primers: constFIS-2F (SEQ ID NO: 33) and GFP-1R (5'-TCAGCTTGCCGTAG-GTGGC-3') (SEQ ID NO: 42).

YFP: annealing 55° C. for 1 min: primers: YFP-2F (5'-ATGGTCCTGCTGGAGTTCG-3') (SEQ ID NO: 43) and hFIS-Exp1R (SEQ ID NO: 38).

Glomyc: annealing 44° C., extension 45 sec at 72° C. Primers: constFIS-2F (SEQ ID NO: 33) and SP6. The recombinants were sequenced by customer-tailored automatic sequencing using the PCR products (Genome Express, Meylan).

b) Subcloning of the hASAP cDNA in a Prokaryotic Expression Vector

Using a strategy similar to that used in paragraph a) above, the hASAP cDNA was cloned into the vector pGEX-4T2 (AMERSHAM), so as to produce a fusion protein with GST, purifiable according to standard protocols.

c) Subcloning of the mASAP cDNA in a Prokaryotic or Eukaryotic Expression Vector Using a strategy similar to that used in paragraph a) above the mASAP cDNA was cloned into the following vectors:

pGEX-4T2 (AMERSHAM), so as to produce a fusion protein with GST, purifiable according to standard protocols.

pEYFP-C1 so as to produce a fusion protein (N-terminal fusion) with the yellow fluorescent protein (YFP) detectable by direct immunofluorescence.

d) Transfection, Immunofluorescence and Microscopy d.1) Materials and Methods

The vectors obtained were transfected according to the calcium phosphate technique or, more routinely, using the jetPEI method (GDSP10101, Qbiogene) according to the producer's recommendations, into the following cell lines:

PEAK (ref. 37937, Edge Biosystems (distributed by Q.BIOgene, Illkirch in France), only for the human ASAP constructs, HEK-293 (ATCC (American Tissue Culture Collection) reference CRL-1573; p 53 −/− non-synchronizable), for the human and murine ASAP constructs, nontransformed NIH3T3 (murine ASAP constructs), and U-2 OS (ATCC HTB-96; p 53+/−, synchronizable).

For vectors 1) and 2) (human and murine ASAP constructs), the localizations were determined directly by detection of the GFP or YFP fluorescence at 24 h, 48 h and 72 h, after fixing of the cells with paraformaldehyde and staining of the nuclei either with propidium iodide or with Hoechst 33286.

For vector 3) the MYC tag was detected using an anti-MYC primary antibody distributed by TEBU (9 E10, cat.#SC-40, Santa Cruz Biotechnology, CA) and an anti-mouse IgG goat secondary antibody labeled with the fluorochrome Alexa-594 (Molecular Probes, ref. A-11032, distributed in France by Interchim, Montluçon), after fixing of the cells and permeabilization thereof with 0.1% Triton X 100. The slides were analyzed, and the images were collected on a Zeiss Axiophot microscope.

d.2) Results: Cellular Localization and Colocalization of the ASAP Protein with Alpha-Tubulin—Cellular Localization FIG. 4 illustrates the cellular localization of the hASAP protein overexpressed in the HEK-293 line (PI=propidium iodide).

Observation under the fluorescence microscope of the slides corresponding to the various transfections with vectors 1), 2) and 3) shows the same types of profile: the localization of the hASAP and mASAP proteins is cytoplasmic and its fibrous profile recalls that of tubulin filaments.

Moreover, it appears that the transfected cells exhibit division deficiencies since the nuclei are always larger than in the nontransfected cells (FIGS. 4A and 4B). In addition, some of the transfected cells appear to be plurinucleated (FIG. 4B). This suggests abnormal division of the transfected cells.

Finally, the mitosis of the transfected cells appears to be abnormal, in terms of both the chromosomal organization and the localization profile of the hASAP and MASAP proteins at the level of the mitotic spindle. The star-shaped localization profile of the hASAP and mASAP proteins is characteristic of the nucleation of the aster microtubules around the centrosome (FIGS. 4C and 4D).

A similar ASAP protein localization profile is detected in the U-2 OS line (p 53 +/−) overexpressing hASAP and in the nontransformed NIH 3T3 line overexpressing MASAP; an accumulation of monopolar cells in mitosis is observed.

In addition, by synchronizing the U-2 OS cells and recovering the cell extracts at various times in the cycle, it was verified that the ASAP protein was indeed present in all the phases of the cell cycle (interphase, S, G2/M).
Colocalization of the ASAP Protein with Alpha-Tubulin FIG. 5 illustrates the colocalization of the human ASAP protein with alpha-tubulin; similarly, the murine ASAP protein colocalizes with alpha-tubulin.

FIG. 5A illustrates the cellular localization of alpha-tubulin detected by immunofluorescence using an anti-tubulin antibody (Alexa-594, Molecular Probe).

FIG. 5B illustrates the localization of the ASAP protein labeled with YFP (yellow fluorescent protein).

FIG. 5C represents the superimposition of the 2 images, demonstrating the colocalization of the 2 proteins.

EXAMPLE 5

Production of anti-hASAP and -mASAP Polyclonal Antibodies a) Antibody Production The following ASAP protein constructs were cloned into the prokaryotic expression vector pGEX 4T-2 (AMERSHAM) as described in example 4:
  whole human ASAP protein (SEQ ID NO: 1),
  human protein from which the C-terminal portion containing the potential MAP domain (residues 1 to 421, SEQ ID NO: 47) has been deleted,
  whole murine protein (SEQ ID NO: 46).

The proteins were expressed in *E. coli* and purified according to standard protocols. Rabbits were then immunized with the purified ASAP proteins according to a standard protocol, and the immune sera were harvested.

b) Analysis of the Reactivity of the Polyclonal Sera with Respect to the Endogenous ASAP Protein The monospecific polyclonal sera directed against the whole hASAP protein or the hASAP protein from which the C-terminal portion containing the potential MAP domain has been deleted were tested by Western blotting and by immunofluorescence, on HEK-293 and U-2 OS cells, according to standard protocols.

By Western blotting, the monospecific polyclonal serum directed against the whole hASAP protein detected a protein having an apparent molecular weight of approximately 110 kDa corresponding to the endogenous ASAP protein, in both the HEK-293 cells and the U-2 OS cells. Under these conditions, an anti-FLAG antibody detected a protein having an equivalent molecular weight, in control HEK-293 or U-2 OS cells, transfected with a vector for expression of the hASAP protein fused with a FLAG tag.

By immunofluorescence, the monospecific polyclonal serum directed against the whole hASAP protein labeled the microtubules of the HEK-293 cells in interphase, the asters of the cells in mitosis and the microtubules of the residual body at the end of telophase.

The monospecific polyclonal serum directed against the hASAP protein from which the C-terminal portion containing the potential MAP domain had been deleted exhibited the same profile by immunofluorescence and detected a protein of approximately 110 kDa, by Western blotting.

The monospecific polyclonal serum directed against the mASAP protein was used to detect which cell types expressed ASAP and at what stage(s) of the cell cycle it was expressed, by immunofluorescence on mouse testicular sections.

EXAMPLE 6

Functional Analysis of the hASAP Protein Using Mutants from which the N-Terminal Portion Containing the BRCT Domain or the C-Terminal Region Containing the Potential Map Domain has Been Deleted Fragments of cDNA encoding an hASAP protein from which the N-terminal portion containing the BRCT domain has been deleted (Ndel1: residues 304-647 (SEQ ID NO: 48); Ndel2: residues 411-647 (SEQ ID NO: 49); Ndel3: residues 478-647 (SEQ ID NO: 50)) or from which the C-terminal portion containing the MAP domain has been deleted (Cdel1: residues 1 to 477 (SEQ ID NO: 51); Cdel2: residues 1 to 418 (SEQ ID NO: 52); Cdel3: residues 1 to 303 (SEQ ID NO: 53)) were amplified by PCR using suitable primers, and then cloned into the expression vectors pEAK10-EGFP (C-terminal fusion with GFP) and pEYFP-C1 (N-terminal fusion with YFP) according to a protocol similar to that described in example 4.

The various constructs were transfected into the HEK-293 and U-2 OS lines, and the cellular localization of the various mutants of the hASAP protein was then analyzed as described in example 4.

It is noted that, for the same deletions, a similar profile is obtained with the construct comprising YFP in the N-terminal position or GFP in the C-terminal position.

By comparison with the whole hASAP protein, the 3 constructs from which the C-terminal portion has been deleted no longer colocalize in interphase with tubulin and no longer have a fibrous appearance; these results indicate that the deletion involves a MAP domain. In addition, no monopolar cell blocked in mitosis is observed in the cells overexpressing the mutants from which the C-terminal portion containing the MAP domain has been deleted.

By comparison with the whole hASAP protein, the three constructs from which the N-terminal portion containing the BRCT domain has been deleted exhibit a nuclear localization in the form of loci, but some fibers colocalizing with tubulin remain in the cytoplasm.

The functional analysis of the hASAP protein is completed by experiments consisting of inactivation of the expression of the gene with interfering RNAs (iRNAs).

The invention claimed is:

1. A method of screening for a substance which activates or inhibits activity of Aster Associated Protein (ASAP) or an ortholog thereof, said substance being selected from the group consisting of a human protein of sequence SEQ ID NO: 1 and proteins having sequences which exhibit at least 80% identity or at least 90% similarity, with an entire sequence SEQ ID NO: 1, wherein intracellular over-expression of said ASAP or an ortholog thereof disturbs organization of a mitotic spindle, wherein said method comprises the steps of:

a) contacting, in a first step, cells of a biological sample expressing said ASAP or an ortholog thereof, with a substance to be tested;

b) measuring in a second step, the effect of said substance on mitotic spindle organization or the rate of induction of aberrant and abortive mitoses;

c) comparing, in a third step, the measured effect of said substance to a previously measured effect in an absence of said substance to determine a relative effect of said substance; and d) selecting, in a fourth step, a substance which activates or inhibits said activity.

2. The method of claim 1, wherein the ASAP protein which is expressed is murine ASAP (SEQ ID NO: 46).

3. The method of claim 1, wherein the cells of the biological sample expressing the ASAP protein are transformed host cells over-expressing a recombinant ASAP protein.

4. The method of claim 3, wherein the recombinant ASAP protein is an ASAP protein fused with a fluorescent protein.

5. The method of claim 1, wherein the substance is a protein having at least 90% identity or at least 95% similarity with an entire sequence SEQ ID NO: 1.

6. The method of claim 1, wherein the substance is a protein having a molecular weight of between 60 and 100 kDa.

7. The method of claim 6, wherein the protein is associated with centrosomes.

8. The method of claim 1, wherein the protein is colocalized, by immunofluorescene, with α-tubulin of microtubules of the mitotic spindle.

9. The method of claim 6, wherein the protein has a molecular weight of 65 and 80 kDa.

* * * * *